US006465203B2

(12) United States Patent
Nichols

(10) Patent No.: US 6,465,203 B2
(45) Date of Patent: *Oct. 15, 2002

(54) GLUCAN-CONTAINING COMPOSITIONS AND PAPER

(75) Inventor: Scott E. Nichols, Johnston, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/740,274

(22) Filed: Dec. 19, 2000

(65) Prior Publication Data

US 2002/0031826 A1 Mar. 14, 2002

Related U.S. Application Data

(60) Division of application No. 09/210,361, filed on Dec. 11, 1998, which is a continuation-in-part of application No. 09/009,620, filed on Jan. 20, 1998, now Pat. No. 6,127,603, and a continuation-in-part of application No. 09/007,999, filed on Jan. 16, 1998, now Pat. No. 6,087,559, and a continuation-in-part of application No. 09/008,172, filed on Jan. 16, 1998, now Pat. No. 6,127,602, which is a continuation of application No. 08/485,243, filed on Jun. 7, 1995, now Pat. No. 5,712,107, and a continuation of application No. 08/478,704, filed on Jun. 7, 1995, now abandoned, and a continuation of application No. 08/482,711, filed on Jun. 7, 1995, now abandoned.

(51) Int. Cl.[7] .............................. C12Q 1/48; C12Q 1/68; C12Q 1/00; C12Q 1/34
(52) U.S. Cl. ................................ 435/15; 435/6; 435/4; 435/18; 435/278; 435/885; 435/886; 435/170; 536/1.11; 536/18.5; 536/123.12; 536/124; 536/128; 800/284
(58) Field of Search ........................... 435/15, 6, 4, 18, 435/278, 885, 886, 170; 536/1.11, 18.5, 123.12, 124, 128; 800/284

(56) References Cited

U.S. PATENT DOCUMENTS

| 4,202,966 A | | 5/1980 | Misaki et al. ............... 536/1.11 |
|---|---|---|---|
| 4,342,601 A | | 8/1982 | Yin ........................ 536/123.12 |
| 4,597,830 A | | 7/1986 | April et al. ............. 536/123.12 |
| 4,734,162 A | | 3/1988 | Ampulski ............... 536/123.12 |
| 5,354,424 A | | 10/1994 | Rha et al. ............... 536/123.12 |
| 5,679,880 A | | 10/1997 | Curtis III et al. ........... 800/205 |
| 5,712,107 A | | 1/1998 | Nichols ................... 435/278.4 |
| 5,712,135 A | | 1/1998 | D'Halluin et al. ........ 435/172.3 |
| 5,985,666 A | | 11/1999 | Loiselle et al. ............. 435/419 |
| 6,087,559 A | * | 7/2000 | Nichols ....................... 800/284 |
| 6,127,602 A | * | 10/2000 | Nichols ....................... 800/284 |
| 6,284,479 B1 | * | 9/2001 | Nichols ......................... 435/15 |

FOREIGN PATENT DOCUMENTS

| GB | 1122354 | 8/1968 |
|---|---|---|
| JP | 06 287 887 | 11/1994 |
| JP | 06 313 297 | 11/1994 |
| WO | WO 94/11520 | 5/1994 |
| WO | WO 95/13389 | 11/1994 |
| WO | WO 96/06173 | 8/1995 |
| WO | WO 96/01904 | 1/1996 |
| WO | WO 97/29186 | 2/1997 |
| WO | WO 97/47806 | 12/1997 |
| WO | WO 97/47808 | 12/1997 |

OTHER PUBLICATIONS

Kuramitsu, et al. "Characterization of Extracellular Glucosyltransferase Activity of *Streptococcus mutans*" *Infection and Immunity*; vol. 12(4); pp. 738–749; (1975).

Yamashita, et al. "Role of the *Streptococcus mutans* gtf Genes in Caries Induction in the Specific–Pathogen–Free Rat Model" *Infection and Immunity*; vol. 61(9); pp. 3811–3817; (1993).

Kametaka, et al. "Purification and characterization of glucosyltransferase from *Streptococcus mutans* OMZ176 with chromatofocusing" *Microbios*; vol. 51; pp. 29–35; (1987).

Aoki, et al. "Cloning of a *Streptococcus mutans* Glucosyltransferase Gene Coding for Insoluble Glucan Synthesis" *Infection and Immunity*; vol. 53(3); pp. 587–595; (1986).

Shimamura, et al. "Identifaction of Amino Acid Residues in *Streptococcus mutans* Glucosyltransferases Influencing the Structure of the Glucan Product" *Journal Bacteriology*; vol. 176 (16); pp. 4845–4850; (1994).

Wenham, et al. "Regulation of Glucosyl—and Fructosyltransferase Synthesis by Continuous Cultures of *Streptococcus mutans*" *J. General Microbiology*; vol. 114; pp. 117–124; (1979).

Fu, et al. "Maltodextrin Acceptor Reactions of *Streptoccus mutans* 6715 Glucosyltransferases" *Carbohydrate Research*; vol. 217; pp. 201–211; (1991).

Bhattacharjee, et al. "Formation of $-(1\rightarrow 6)$, $-(1\rightarrow 3)$, and $-(1\rightarrow 2)$ Glycosidic Linkages by Dextransucrase from *Streptoccus sanguis* in Acceptor–Dependent Reactions" *Carbohydrate Research*; vol. 242; pp. 191–201; (1993).

Russell, et al. "Expression of a Gene for Glucan–binding Protein from *Streptococcus mutans* in *Escherichia coli*" *J. General Microbiology*; vol. 131; pp. 295–299; (1985).

Russell, et al. "Characterization of Glucosyltransferase Expressed from a *Streptococcus sobrinus* Gene Cloned in *Escherichia coli*" *J. General Microbiology*; vol. 133; pp. 935–944; (1987).

(List continued on next page.)

Primary Examiner—Louise N. Leary
(74) Attorney, Agent, or Firm—Pioneer Hi–Bred International, Inc.

(57) ABSTRACT

The present invention provides methods of making paper, utilizing glucans, produced by the glucosyltransferase B, C or D enzyme of the species *Streptococcus mutans*, instead of modified starches. The present glucans are functionally similar to currently utilized modified starches and are particularly useful in the coating step of paper manufacture. The present glucans also exhibit thermoplastic properties and impart gloss to the paper during the coating step.

34 Claims, No Drawings

OTHER PUBLICATIONS

Shiroza, et al. "Sequence Analysis of the *gtfB* Gene from *Streptococcus mutans*" *J. Bacteriology;* vol. 169(9); pp. 4263–4270; (1987).

Müller–Röber, et al. "Inhibition of the ADP–glucose pyrophosphorylase in transgenic potatoes leads to sugar–storing tubers and influences tuber formation and expression of tuber storage protein genes" *The EMBO J.;* vol. 11(4); pp. 1229–1238; (1992).

Creech, et al. "Carbohydrate Synthesis in Maize" *Advances in Agronomy;* vol. 20; pp. 275–322; (1968).

Utsumi, et al. "Expression and Accumulation of Normal and Modified Soybean Glycinins in Potato Tubers" *Plant Science;* vol. 102; pp. 181–188; (1994).

Visser, et al. "Transformation of Homozygous Diploid Potato with an *Agrobacterium tumefacies* Binary Vector System by Adventitious Shoot Regeneration on Leaf and Stem Segments" *Plant Molecular Biology;* vol. 12; pp. 329–337; (1989).

Ebskamp, et al. "Accumulation of Fructose Polymers in Transgenic Tobacco" *Bio/Technology;* vol. 12; pp. 272–275; (1994).

Armstrong, et al. "Regeneration of Plants from Somatic Cell Cultures: Application for *in vitro* Genetic Manipulation" *The Maize Handbook;* pp. 663–671; (1994).

Heiser, et al. "Starch Formulations" *Starch and Starch Products in Paper Coating;* pp. 147–162; (1990).

Honda, O., *et al.* "Nucleotide sequence of the *Streptococcus mutans* gtfD gene encoding the glucosyltransferase–S enzyme" J. of General Microbiology (1990) 136, 2099–2105.

Napoli et al. "Introduction of a Chimeric Chalcone Synthase Gene into Petunia Results in Reversible Co–Suppression of Homologous Genes *in trans*" The Plant Cell (Apr. 1990) 2, 279–289.

von Schaewen et al. "Expression of a yeast–derived invertase in the cell wall of tobacco and *Arabidopsis* plants leads to accumulation of carbohydrate and inhibition of photosynthesis and strongly influences growth and phenotype of transgenic tobacco plants" The EMBO Journal (1990) vol. 9 No. 10, pp. 3033–3044.

Kossman, et al. "Transgenic plants as a tool to understand starch biosynthesis" Carbohydrate Bioengineering (1995), Petersen et al., eds., Elsevier Science, pp. 271–278.

Ueda et al. Sequence analysis of the *gtfC* gene from *Streptococcus mutans* GF–5, Gene 69 (1988) pp. 101–109.

Guan, H.P. et al. "Expression of Branching Enzyme I of Maize Endosperm in *Escherichia coli*" (1994) Plant Physiology 104: 1649–1453.

Hanada, et al. "Isolation and Characterization of the *Streptococcus mutans gtfC* Gene, Coding for Synthesis of Both Soluble and Insoluble Glucans" *Infection and Immunity;* vol. 56(8); pp. 1999–2005;(1998).

Creech, et al. "Carbohydrate Synthesis in Maize" *Advances in Agronomy;* vol. 20; pp. 275–322; (1968).

Gordon–Kamm, et al. "Transformation of Maize Cells and Regeneration of Fertile Transgenic Plants" *The Plant Cell;* vol. 2; pp. 603–618; (1975).

Gordon–Kamm, et al. "Transformation of Maize using Microprojectile Bombardment: An Update and Perspective" *In Vitro Cellular and Developmental Biology Plant 27P;* vol. 1; pp. 21–27; (1991).

Walbot & Messing "Gene Expression in Corn" *Corn and Corn Improvement;* Sprague and Dudley editors. $3^{rd}$ edition (1988).

Schopke, et al. "Transformation in Cassava" *Biotechnology in Agriculture and Forestry;* vol. 23; pp. 273–289 (1993).

Lowe, et al. "Genetic Transformation in *Ipomoea batatas* (L.) Lam (Sweet Potato)" *Biotechnology in Agriculture and Forestry,* vol. 29; pp. 308–320 (1994).

Juboory, et al. "*In Vitro* Regeneration of Agrobacterium–Transformed Sweet Potato (*Ipomoea batatas* L.)"*PGRSA Quaterly;* vol. 19, No. 2, pp. 82–89 (1991).

Prakash, et al. "Genetic transformation of sweet potato by particle bombardment" *Plant Cell Reports;* vol. 11, pp. 53–57 (1992).

Chen, et al. "Transformation of sugarcane protoplasts by direct uptake of a selectable chmaeric gene" *Plant Cell Reports;* vol. 6, pp. 297–301 (1987).

Weising et al. "Foreign Genes in Plants: Transfer, Structure, Expression, and Applications" *Annual Rev. Genetic;* vol. 22, pp. 421–477 (1988).

Birch, et al. "Transformation of Sugarcane" *Biotechnology in Agriculture and Forestry;* vol. 23; pp. 348–360 (1993).

Chowdhury, et al. "Stably transformed herbicide resistant callus of sugarcane via microprojectile bombardment of cell suspension cultures and electroporation of photoplasts" *Plant Cell Reports;* vol. 11; pp. 494–498.

Xu–Yao, et al. "Interaction and Transformation of Cereal Cells with Phenolics pretreated *Agrobacterium tumefaciens*" *Chinese J. Bot.;* vol. 2 (2); pp. 81–87.

Fromm, et al. "Inheritance and Expression of Chimeric Genes in the Progeny of Transgenic Maize Plants" *Bio/Technology;* vol. 8; pp. 833–839.

\* cited by examiner

GLUCAN-CONTAINING COMPOSITIONS AND PAPER

CROSS REFERENCE

This application is a divisional of U.S. patent application No. 09/210,361 filed Dec. 11, 1998, which was a CIP of U.S. application Nos. 09/009,620 filed Jan. 20, 1998 (now U.S. Pat. No. 6,127,603), 09/007,999 filed Jan. 16, 1998 (U.S. Pat. No. 6,087,559) and 09/008,172 filed Jan. 16, 1998 (U.S. Pat. No. 6,127,602) which, respectfully, are a continuation of U.S. patent application No. 08/485,243, (U.S. Pat. No. 5,712, 107) 08/478,704, and 08/482,711, all filed Jun. 7, 1995, now abandoned, all of which are incorporated by reference herewithin in their entirety.

Sequence Listing

Seq ID No. 1—a gtfb cDNA sequence
Seq ID No. 2—the GTFB protein sequence encoded by Seq ID No.1
Seq ID No. 3—a gtfc cDNA sequence
Seq ID No. 4—the GTFC protein sequence encoded by Seq ID No. 3
Seq ID No. 5—a gtfd cDNA sequence
Seq ID No. 6—the GTFD protein sequence encoded by Seq ID No. 5

FIELD OF THE INVENTION

The present invention involves the field of paper manufacture. Specifically, the present invention provides sources alternative to modified starch in paper manufacture.

BACKGROUND OF THE INVENTION

There are three major phases in paper manufacture where starch is used as an ingredient. The first is the "wet end" where cellulose fibers are mixed with starch in a slurry, and the slurry is forced through a narrow opening onto a wire belt. Water is rapidly removed as the forming sheet travels the length of the belt. After a distance of typically five to fifteen meters on the belt, the sheet has had enough water removed from it so that it can support its own weight. The sheet travels through a number of foils and rolls wherein more water is removed. It is dried to about 11% moisture.

The second phase in paper manufacturing involving starch is the "sizing step". Here, the paper goes through a sizing press where a slurry including starch is applied to the sheet. The sheet again goes through a series of foils and rolls. It is dried on rollers and can be taken off the press as a finished product.

The third step involves coating the paper with a mixture of starch and a thermoplastic molecule. On certain lines, this occurs after the sizing step. The nascent roll can also be removed and reinstalled onto a different press for coating. A typical coating device has two blades that run the width of the paper. The blades apply the coating material onto two rolling drums. The paper passes between the drums and the coating material, comprising starch and the thermoplastic moiety, comes off the drums onto the paper. After the paper leaves the drums, it goes through a number of dryers. When the paper is dry, it goes onto a "soft calendar" comprising two drums, one made of a hard density fabric and the other a heated steel drum. The paper passes between the two drums and the heated steel drum is sufficiently hot to melt thermoplastic components of the coating mix providing a hard gloss finish on the paper.

The cellulosic wood pulp fibers, typically used in the above process, are anionic in nature. The addition of a cationic starch to the "wet end" slurry acts as an adhesive by cross linking the pulp fibers through salt linkages. Thus a cross linked polymeric network is made, comprising the starch and cellulose fibers. Typically, the cationic starches used in the "wet end" contain tertiary or quaternary amines. These amino groups are added to the starch following the wet milling process.

Surface sizing starches are used to impart both strength and smooth finish to the sheet after it leaves the "wet end". Such starches also prepare the sheet to receive the various coatings. In cheaper grades of paper and in fiberboard manufacture, sizing starches are used simply as unmodified corn starch. For high grades of paper, chemically-modified starches are used. This is important for the application of a smooth, uniform high quality surface to the paper.

There is a tendency for starches to retrograde i.e. re-form high ordered structures (both helices and crystallites) in an otherwise gelatinous starch slurry. Deposition of retrograded starch onto high quality paper causes regional inconsistencies on the paper and is unacceptable. Furthermore, retrograded starch in the sizing press may necessitate shutting the line down to clear the apparatus.

The starch most often used for sizing applications is a starch having a covalently attached neutral adduct, for instance hydroxyethyl starch. This is prepared by the reaction of ethylene oxide with starch after it is isolated at the wet milling plant. The function of the hydroxyethyl (or similar) adduct is independent of its chemical nature; rather, it serves to provide steric hindrance, inhibiting the formation of high ordered structures. This steric hindrance is critical to decrease retrogradation. The periodic protuberance afforded by the adduct disrupts the formation of higher ordered structures that leads to retrogradation.

Speed is of paramount importance in paper manufacturing. What limits press speed is the requirement to remove water. With a higher concentration of starch, there would be less water to remove, and the press could run at higher speed. However, higher concentrations of starch accelerate retrogradation and retrograded starch deposition onto the sheet and as noted above is unacceptable.

Hydroxethylated starch also forms higher ordered structures as the temperature decreases or the concentration increases. The formation of the higher ordered structures on the surface of the paper is required. After application to the sheet the starch reforms some of these higher ordered structures and creates a uniform surface that imparts structural strength and facilitates the acceptance of inks and dyes. However, the higher ordered structures should not form in the slurry nor on the application device because this necessitates shutting down the production line to clear off retrograded starch.

The function of the hydroxyethyl group is to lower the temperature and/or raise the concentration of starch at which retrogradation occurs. As the processing lines have already been optimized for a particular temperature of the starch slurry, a decrease in the tendency to retrograde would allow for a higher carbohydrate content in the slurry.

The mixture applied to the paper sheet in the coating process contains hydroxethylated starch and thermoplastic molecules. The most prevalent thermoplastic molecules used are latexes, such as styrene butadiene. The function of the hydroxethyl starch is as indicated above. The function of the thermoplastic molecule is to form a high gloss finish on the paper. This causes an increased ability to take inks and dyes and improves the resolution, in general, on the printed sheet.

Based on the foregoing, there exists a need, in paper manufacturing, for modified starch substitutes which are functionally similar to modified starch. There is a further need to provide substitutes for modified starch which are less prone to retrogradation. There is a further need to provide methods of manufacturing paper which are faster than current methods and allow presses to run closer to their full capacity speed. There is a further need to provide methods of manufacturing paper that are environmentally-friendly and do not involve input materials that require chemical processing. Meeting these needs would advance the state of science and industry in this area.

SUMMARY OF THE INVENTION

It is an object of the present invention to provide methods for manufacturing paper using glucans.

It is another object of the present invention to provide a method of imparting gloss during paper manufacture.

It is another object of the present invention to provide nucleic acids and polypeptides relating to substitutes for starch in paper manufacturing.

It is another object of the present invention to provide transgenic plants and plant parts containing the proteins of the present invention.

It is another object of the present invention to provide transgenic plants and plant parts containing the nucleic acids of the present invention.

Therefore, in one aspect, the present invention relates to an isolated nucleic acid comprising a member selected from the group consisting of:

a polynucleotide which encodes a polypeptide of gtfb having changes at positions selected from the group consisting of I448V; D457N; D567T; K1014T; D457N/D567T; D457N/D571K; D567T/D571K; D567T/D571K/K1014T; I448V/D457N/D567T/D571K/K779Q/K1014T; Y169A/Y170A/Y171A; and K779Q;

a polynucleotide which encodes a polypeptide of gtfd having changes at positions selected from the group consisting of T589D; T589E; N471D; N471D/T589D; and N471D/T589E;

a polynucleotide complementary to a polynucleotide of (a) or (b).

Therefore, in another aspect, the present invention relates to an isolated protein comprising a member selected from the group consisting of:

a polypeptide comprising at least 20 contiguous amino acids in a polypeptide of gtfb having changes at positions selected from the group consisting of I448V; D457N; D567T; K1014T; D457N/D567T; D457N/D571K; D567T/D571K; D567T/D571K/K1014T; I448V/D457N/D567T/D571K/K779Q/K1014T; Y169A/Y170A/Y171A; and K779Q;

a polypeptide comprising at least 20 contiguous amino acids in a polypeptide of gtfd having changes at positions selected from the group consisting of T589D; T589E; N471D; N471D/T589D; and N471D/T589E;

a polypeptide comprising at least 50% sequence identity to the nucleic acid of claim 1, wherein the % sequence identity is based on the entire sequence and is determined by GAP analysis using Gap Weight of 12 and Length Weight of 4;

a polypeptide encoded by the nucleic acid of claim 27;

a polypeptide encoded by the nucleic acid of gtfb having changes at positions selected from the group consisting of I448V; D457N; D567T; K1014T; D457N/D567T; D457N/D571K; D567T/D571K; D567T/D571K/K1014T; I448V/D457N/D567T/D571K/K779Q/K1014T; Y169A/Y170A/Y171A; and K779Q; and a polypeptide encoded by the nucleic acid of gtfd having changes at positions selected from the group consisting of T589D; T589E; N471D; N471D/T589D; and N471D/T589E.

DETAILED DESCRIPTION OF THE INVENTION

The present invention provides glucans which can be used as substitutes for and additions to modified starch and latexes in paper manufacture. The glucans of the present invention are produced by the glucosyltransferase B ("GTF B"), glucosyltransferase C ("GTF C"), and glucosyltransferase D ("GTF D") enzymes, encoded by genes, alleles and mutations of gtfb, gtfc and gtfd. The present invention also includes gtf genes and GTF proteins with sequence identity, fragments, deletions, truncations, insertions and substitutions of the GTF proteins and genes of the species *Streptococcus mutans* that are functionally similar to the modified starch currently used in paper manufacture. The present glucans also exhibit similar physical properties to thermoplastic molecules currently used in the coating step during paper manufacture.

The present invention also provides methods of making paper utilizing the present glucans, input materials that are produced biologically. Thus, the present methods are more cost-effective and environmentally friendly than current methods, which require input materials that produce chemical effluents.

DEFINITIONS

As used herein "glucan" means a glucose polymer having linkages that are predominantly (1→3), (1→6) with branch points occurring at (1→3, 6). Minor linkages at (1→2) and (1→4).

As used herein "amyloplast" means starch accumulating organelle in plant storage tissue.

As used herein, "vacuole" means the cellular compartment bounded by the tonoplast membrane.

The term "isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

As used herein, "polypeptide" means proteins, protein fragments, modified proteins, amino acid sequences and synthetic amino acid sequences. The polypeptide can be glycosylated or not.

As used herein, "plant" includes but is not limited to plant cells, plant tissue and plant seeds.

As used herein, "promoter" includes reference to a region of DNA upstream from the start of transcription and involved in recognition and binding of RNA polymerase and other proteins to initiate transcription.

By "fragment" is intended a portion of the nucleotide sequence or a portion of the amino acid sequence and hence protein encoded thereby. Fragments of a nucleotide sequence may encode protein fragments that retain the biological activity of the native nucleic acid. Alternatively, fragments of a nucleotide sequence that are useful as hybridization probes generally do not encode fragment proteins retaining biological activity. Thus, fragments of a nucleotide sequence are generally greater than 10 nucleotides, preferably at least 20 nucleotides and up to the entire nucleotide sequence encoding the proteins of the invention. Generally the probes are less than 1000 nucleotides and preferably less than 500 nucleotides. Fragments of the invention include antisense sequences used to decrease expression of the inventive genes. Such antisense fragments may vary in length ranging from at least about 20 nucleotides, about 50 nucleotides, about 100 nucleotides, up to and including the entire coding sequence.

By "variants" is intended substantially similar sequences.

Generally, nucleic acid sequence variants of the invention will have at least 70%, preferably 80%, more preferably at least 90% and most preferably at least 95% sequence identity to the native nucleotide sequence as determined by homology algorithms such as described below.

Generally, polypeptide sequence variants of the invention will have at least about 80%, preferably at least about 90%, and more preferably at least about 95% sequence identity to the native protein.

As used herein, "sequence identity" or "identity" in the context of two nucleic acid or polypeptide sequences includes reference to the residues in the two sequences that are the same when aligned for maximum correspondence over a specified comparison window. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions which are not identical may differ by conservative amino acid changes.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 575 Science Dr., Madison, Wisconsin, USA; the CLUSTAL program is well described by Higgins and Sharp, *Gene* 73:237–244 (1988); Higgins and Sharp, *CABIOS* 5: 151–153 (1989); Corpet et al., *Nucleic Acids Research* 16:10881–90 (1988); Huang et al., *Computer Applications in the Biosciences* 8:155–65 (1992), and Pearson et al., *Methods in Molecular Biology* 24:307–331 (1994).

Also useful are the BLAST 2.0 suite of programs using default parameters. Altschul et al., *Nucleic Acids Res.* 25:3389–3402 (1997). Software for performing BLAST analyses is publicly available, e.g., through the National Center for Biotechnology Information (hftp://www.ncbi.nlm.nih.gov/).

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel et al., Eds., Greene Publishing and Wiley-lnterscience, New York (1995).

By "functionally equivalent" is intended that the sequence of the variant defines a polynucleotide that encodes a protein having substantially the same biological effect as the native protein of interest.

The wild type nucleic acids encoding GTF B, GTF C and GTF D enzymes are useful in producing glucans according to the present invention. The glucans produced are particularly useful as substitutes for modified starches in the coating step of paper manufacture. The present glucans are also useful as substitutes for thermoplastic molecules such as latex (e.g. styrene butadiene). The subject glucans impact a high gloss finish on the paper and increase the ability of the paper to take on dyes and inks and improves the resolution in general on the printed sheet.

*Streptococcus mutans* is a species that is endogenous to the oral cavity and colonizes tooth enamel. See e.g. Kuramitsu et al., "Characterization of Extracellular Glucosyl Transferase Activity of *Streptococcus-mutans*," *Infect Immun.;* Vol. 12(4); pp. 738–749; (1975); and Yamashita et al., "Role of the *Streptococcus-Mutans*-gtf Genes in Caries Induction in the Specific-Pathogen-Free Rat Model," *Infect. Immun.;* Vol. 61(9); pp. 3811–3817; (1993); both incorporated herein their entirety by reference. *Streptococcus mutans* species secrete the glucosyltransferase B, C and D ("GTF B, C and D") enzymes, which utilizes dietary sucrose to make a variety of extracellular glucans. See e.g. Shiroza et al., "Sequence Analysis of the gtfb Gene from *Streptococcus mutans*," *J. Bacteriol.;* Vol. 169(9); pp. 4263–4270; (1987); Hanada et al., "Isolation and Characterization of the *Streptococcus mutans* gtfc Gene, Coding for Synthesis of Both Soluble and Insoluble Glucans," *Infect. Immun.;* Vol. 56(8); pp. 1999–2005; (1988); Honda et al., "Nucleotide Sequence of the *Streptococcus mutans* gtfD Gene Encoding the Glucosyltransferase-S Enzyme" J. Gen. Microbiol. Vol. 136 pp 2099–2105; and Kametaka et al., "Purification and Characterization of Glucosyltransferase from *Streptococcus-mutans* OMZ176 with Chromatofocusing," *Microbios;* Vol. 51(206); pp. 29–36; (1978); both incorporated herein in its entirety by references.

*Streptococcus sobrinus* is a serotype of *Streptococcus mutans* and included in this invention. One of skill in the art will recognize that other glucans can be utilized in the present invention such as *S. sanguis, S. rattus. S. milleri, S. bovis, S. oralis, S. gordonii* and *S. salivarius.*

Both soluble and insoluble glucans are synthesized, and the proteins responsible have been isolated and characterized. See e.g. Aoki et al., "Cloning of a *Streptococcus-mutans* Glucosyltransferase Gene Coding for Insoluble Glucan Synthesis" *Infect. Immun.,* Vol. 53 (3); pp. 587–594; (1986); Shimamura et al., "Identification of Amino Acid Residues in *Streptococcus mutans* Glucosyltransferases Influencing the Structure of the Glucan Produced," *J. Bacteriol.;* Vol.176(16); pp. 4845–50; (1994); and Kametaka et al., "Purification and Characterization of Glucosyltransferase from *Streptococcus-mutans* OMZ176 with Chromatofocusing," *Microbios;* Vol. 51 (206); pp. 29–36; (1987); all incorporated herein their entirety by reference.

The proteins involved are large (~155 kDa) and catalyze the group transfer of the glucosyl portion of sucrose to an acceptor glucan predominantly via (1→3) and (1→6) linkages. See e.g. Wenham et al., "Regulation of Glucosyl Transferase and Fructosyl Transferase Synthesis by Continuous Cultures of *Streptococcus-mutans*," *J. Gen Microbiol.;* Vol. 114 (Part 1); pp. 117–124; (1979); and Fu et al., "Maltodextrin Acceptor Reactions of *Streptococcus-mutans* 6715 glucosyltransferases," *Carbohydr. Res.;* Vol. 217; pp. 210–211; (1991); and Bhattacharjee et al., "Formation of Alpha—(1→6), Alpha—(1→3), and Alpha (1→2) Glycosidic Linkages by Dextransucrase from *Streptococcus Sanguis* in Acceptor-Dependent Reactions," *Carbohydr. Res.,* Vol. 242; pp.191–201; (1993); all incorporated herein their entirety by reference.

The genes involved in glucan synthesis have been isolated and sequenced. See Shimamura et al., cited hereinabove and Russell et al., "Expression of a Gene for Glucan-binding Protein from *Streptococcus-mutans* in *Eschericia-coli*," *J. Gen. MicrobioL;* Vol. 131(2); pp.295–300; (1985); Russell et al., "Characterization of Glucosyltransferase Expressed from a *Streptococcus-Sobrinus* Gene Cloned in *Escherichia-coli*," *J. Gen. Microbiol.;* Vol.133(4); pp. 935–944; (1987); and Shiroza et al., "Sequence Analysis of the gtfb Gene from *Streptococcus mutans*," *J. Bacteriol.;* Vol.169(9); pp. 4263–4270; (1987); all incorporated herein in their entirety by reference. Ueda et al, "Sequence Analysis of the gtfc Gene from *Streptococcus mutans* GF-S, Gene 69 (1988) pp.101–109.

The structure of the glucans produced by the GTF B, C and D enzymes is quite heterogeneous with respect to the proportions of (1→3), (1→6) and (1→3,6) branches present in any given glucan. Transformation of genes that encode naturally occurring GTF B, GTF C or GTF Ds into plants, such as maize, provides novel compositions.

GTF B, GTF C or GTF D enzyme expression or activity in the amyloplast and/or vacuole leads to the accumulation of starch and glucan in the same amyloplast and/or vacuole. Retrogradation occurs as portions of starch molecules interact and subsequently form inter- or intra-chain helices. In a mixture of starch and glucans, the frequency of starch-starch interactions that lead to helix formation is diminished. A paste made from the mixed polymers is less prone to retrogradation as a result. This should be especially true in the starch accumulation mutants envisioned as transformation targets where the relative proportion of starch is reduced.

In a highly preferred embodiment of the present invention, maize lines deficient in starch biosynthesis are transformed with gtfb, gtfc and gtfc genes. Such lines may be like naturally occurring maize mutants (i.e. $sh_2$, $bt_2$, $bt_1$). Transgenic maize may be engineered so as to accumulate lower amounts of starch in the endosperm than does wild type maize See e.g. Müller-Röber et al., "Inhibition of the ADP-glucose Pyrophosphorylase in Transgenic Potatoes Leads to Sugar-Storing Tubers and Influences Tuber Formation and Expression of Tuber Storage Protein Genes," *The EMBO Journal;* Vol. 11 (4); pp. 1229–1238; (1992); and Creech, "Carbohydrate Synthesis in Maize," *Advances in Agronomy;* Vol. 20; pp. 275–322; (1968); both incorporated herein in their entirety by reference. Naturally occurring or genetically engineered maize mutants may be identified by molecular techniques known in the art. Such as antisense, mutation, aptamer or other ways known in the art. Putative gene candidates involved in reduced starch biosynthesis are phosphoglucomutase, starch synthase, starch branching enzymes and others well know in the art.

Glucans produced in transgenic maize by the expression of GTF B, GTF C and GTF D enzymes can function in paper processing without chemical modification, as required of starch. The polymer solution consequently has altered rheological properties and is less prone to retrogradation compared to starch. The glucans are branched and irregular and able to supplant modified starches with comparable or superior efficacy. They do not require any costly chemical modification as does starch. For coating applications, the present glucans exhibit thermoplastic properties in addition to the above advantages.

The nomenclature used below to define the mutant GTF B and GTF D enzymes is as follows: the amino acid position in the polypeptide chain is determined using the start methionine as position 1; the first letter refers to the amino acid in the wild type enzyme; the second letter refers to the amino acid in the mutated enzyme; and enzymes with multiple mutations have each mutation separated by /.

The wild type GTF B and GTF D and mutants thereof useful in producing glucans according to the present invention are provided below. The following code is employed:

| Amino Acid | One-letter Symbol |
|---|---|
| Alanine | A |
| Asparagine | N |
| Aspartic Acid | D |
| Glutamine | Q |
| Glutamic Acid | E |
| Isoleucine | I |
| Lysine | K |
| Threonine | T |
| Tyrosine | Y |
| Valine | V |

The mutant GTF B enzyme used to produce glucans for paper coating is preferably selected from the group consisting of wild type; I448V; D457N; D567T; K1014T; D457N/D567T; D457N/D571K; D567T/D571K; D567T/D571K/K1014T; I448V/D457N/D567T/D571K/K779Q/ K1014T; Y169A/Y170A/Y171A; and K779Q. The mutant GTF B enzyme used to produce glucans for paper coating is more preferably selected from the group consisting of I448V; K1014T; D567T/D571K/K1014T; I448V/D457N/D567T/D571K/K779Q/K1014T; and Y169A/Y170A/Y171A.

The mutant GTF B enzyme used to produce glucans for paper coating is even more preferably selected from the group consisting of K1014T; I448V/D457N/D567T/D571K/K779Q/K1014T; and Y169A/Y170A/Y171A.

The mutant GTF B enzyme used to produce glucans for paper coating is most preferably I448V/D457N/D567T/D571K/K779Q/K1014T; or Y169A/Y170A/Y171A.

The mutant GTF B enzyme used to produce glucans for paper sizing is preferably selected from the group consisting of 1448V; D457N; D567T; K779Q; K1014T; D457N/D567T; D457N/D571K; D567T/D571K and D567T/D571K/K1014T.

The mutant GTF B enzyme used to produce glucans for paper sizing is more preferably selected from the group consisting of I448V; D457N: K779Q; D567T/D571K; and D567T/D571K/K1014T.

The mutant GTF B enzyme used to produce glucans for paper sizing is most preferably I448V.

The mutant GTF D enzymes used to produce glucans for paper coating are preferably selected from the group consisting of; the wild type of the enzyme; T589D; T589E; N471D; N471D/T589D; and N471D/T589E; more preferably from the group consisting of the wild type; N471D;

N471D/T589D; and N471D/T589E; even more preferably from the group consisting of the wild type and N471D. The wild type of the enzyme is the most preferred.

The mutant GTF D enzymes used to produce glucans for paper sizing are preferably selected from the group consisting of the wild type of the enzyme; T589D; T589E; N471D; N471D/T589D; and N471D/T589E; more preferably from the group consisting of N471D; N471D/T589D; and N471D/T589E; most preferably N471D.

Nucleic Acids

The glucans of the present invention are produced by the glucosyltransferase B ("GTF B"), glucosyltransferase C ("GTF C"), and glucosyltransferase D ("GTF D") enzymes, encoded by genes, alleles and mutations of gtfb, gtfc and gtfd. The present invention also includes gtf genes and GTF proteins with "sequence identity, fragments, deletions, truncations, insertions and substitutions of the GTF proteins and genes of the species Streptococcus mutans that are functionally similar to the modified starch currently used in paper manufacture. For example see "Glucosyltransferase gene polymorphism among Streptococcus mutans strains" CHIA-J-S; HSU-T-Y; TENG-L-J; CHEN-J-Y; HAHN-L-J; YANG-C-S, INFECTION AND IMMUNITY 59(5): 1656–1660,1991 and "Analysis of a DNA polymorphic region in the gtfB and gtfc genes of Streptococcus mutans" CHIA-J-S; LIN-S-W; HSU-T-Y; CHEN-J-Y; KWAN-H-W; YANG-C-S, INFECTION AND IMMUNITY 61(4): 1563–1566, 1993.

Most deletions, insertions and substitutions of the protein sequence are not expected to produce radical changes in the characteristics of the protein. However, when it is difficult to predict the exact effect of the substitution, deletion or insertion in advance of doing so, one skilled in the art will appreciate that the effect will be evaluated by routine screening assays such as the proteins and genes of the invention may be altered in various ways, as indicated above, and methods for such manipulations are generally known in the art. See, for example, Kunkel, T. (1985) Proc. Natl. Acad. Sci. USA 82:488–492: Kunkel et al. (1987) Methods in Enzymol. 154:367–382: U.S. Pat. No. 4,873,192; Walker and Gaastra (eds.) Techniques in Molecular Biology, MacMillan Publishing Company, N.Y. (1983). It is further recognized that component polypeptides or fragments of the proteins may be produced which retain activity. These fragments include truncated sequences, as well as N-terminal, C-terminal, internal and internally deleted amino acid sequences of the proteins.

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot or dicot. In preferred embodiments the monocot is corn, sorghum, barley, wheat, millet, or rice. Preferred dicots include soybeans, sunflower, canola, alfalfa, potato, sugar beet or cassava.

Functional fragments included in the invention can be obtained using primers that selectively hybridize under stringent conditions. Primers are generally at least 12 bases in length and can be as high as 200 bases, but will generally be from 15 to 75, preferably from 15 to 50. Functional fragments can be identified using a variety of techniques such as restriction analysis, Southern analysis, primer extension analysis, and DNA sequence analysis.

The present invention includes a plurality of polynucleotides that encode for the identical amino acid sequence. The degeneracy of the genetic code allows for such "silent variations" which can be used, for example, to selectively hybridize and detect allelic variants of polynucleotides of the present invention. Additionally, the present invention includes isolated nucleic acids comprising allelic variants. The term "allele" as used herein refers to a related nucleic acid of the same gene.

Variants of nucleic acids included in the invention can be obtained, for example, by oligonucleotide-directed mutagenesis, linker-scanning mutagenesis, mutagenesis using the polymerase chain reaction, and the like. See, for example, Ausubel, pages 8.0.3–8.5.9. Also, see generally, McPherson (ed.), DIRECTED MUTAGENESIS: A Practical approach, (IRL Press, 1991). Thus, the present invention also encompasses DNA molecules comprising nucleotide sequences that have substantial sequence similarity with the inventive sequences.

Variants included in the invention may contain individual substitutions, deletions or additions to the nucleic acid or polypeptide sequences which alters, adds or deletes a single amino acid or a small percentage of amino acids in the encoded sequence is a "conservatively modified variant" where the alteration results in the substitution of an amino acid with a chemically similar amino acid. When the nucleic acid is prepared or altered synthetically, advantage can be taken of known codon preferences of the intended host.

The present invention also includes nucleic acids produced by DNA sequence shuffling of the inventive polynucleotides to obtain a desired characteristic. Sequence shuffling is described in PCT publication No. 96/19256. See also, Zhang, J.- H. et al., Proc. Natl. Acad. Sci. USA 94:4504–4509 (1997).

The present invention also includes the use of 5' and/or 3' untranslated regions (UTR) regions for modulation of translation of heterologous coding sequences. Positive sequence motifs include translational initiation consensus sequences (Kozak, Nucleic Acids Res. 15:8125 (1987)) and the 7-methylguanosine cap structure (Drummond et al., Nucleic Acids Res. 13:7375 (1985)). Negative elements include stable intramolecular 5' UTR stem-loop structures (Muesing et al., Cell 48:691 (1987)) and AUG sequences or short open reading frames preceded by an appropriate AUG in the 5' UTR (Kozak, supra, Rao et al., Mol and Cell. Biol. 8:284 (1988)).

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., Nucleic Acids Res. 12:387–395 (1984)) or MacVector 4.1 (Eastman Kodak Co., New Haven, Conn.).

For example, the inventive nucleic acids can be optimized for enhanced expression in plants of interest. See, for example, EPA0359472; WO91/16432; Perlak et al. (1991) Proc. Natl. Acad. Sci. USA 88:3324–3328; and Murray et al. (1989) Nucleic Acids Res. 17:477–498. In this manner, the genes can be synthesized utilizing plant-preferred codons. See, for example, Murray et al. (1989) Nucleic Acids Res. 17:477–498, the disclosure of which is incorporated herein by reference.

The present invention provides subsequences comprising isolated nucleic acids containing at least 16 contiguous bases of the inventive sequences. For example the isolated nucleic acid includes those comprising at least 16, 20, 25, 30, 40, 50, 60, 75 or 100 contiguous nucleotides of the inventive sequences. Subsequences of the isolated nucleic acid can be used to modulate or detect gene expression by introducing into the subsequences compounds which bind, intercalate, cleave and/or crosslink to nucleic acids.

The nucleic acids of the invention may conveniently comprise a multi-cloning site comprising one or more endonuclease restriction sites inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention.

A polynucleotide of the present invention can be attached to a vector, adapter, promoter, transit peptide or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known and extensively described in the art. For a description of such nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

The isolated nucleic acid compositions of this invention, such as RNA, cDNA, genomic DNA, or a hybrid thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library.

Exemplary total RNA and mRNA isolation protocols are described in *Current Protocols in Molecular Biology,* Ausubel, et al., Eds., Greene Publishing and Wiley-lnterscience, New York (1995). Total RNA and mRNA isolation kits are commercially available from vendors such as Stratagene (La Jolla, Calif.), Clonetech (Palo Alto, Calif.), Pharmacia (Piscataway, N.J.), and 5'-3' (Paoli, Pa.). See also, U.S. Pat. Nos. 5,614,391; and, 5,459,253.

Typical cDNA synthesis protocols are well known to the skilled artisan and are described in such standard references as: *Current Protocols in Molecular Biology,* Ausubel et al., Eds., Greene Publishing and Wiley-lnterscience, New York (1995). cDNA synthesis kits are available from a variety of commercial vendors such as Stratagene or Pharmacia.

An exemplary method of constructing a greater than 95% pure full-length cDNA library is described by Carninci et al., *Genomics,* 37:327–336 (1996). Other methods for producing full-length libraries are known in the art. See, e.g., Edery et al., *Mol. Cell Biol.* 15(6):3363–3371 (1995); and, PCT Application WO 96/34981.

It is often convenient to normalize a cDNA library to create a library in which each clone is more equally represented. A number of approaches to normalize cDNA libraries are known in the art. Construction of normalized libraries is described in Ko, *Nucl. Acids. Res.* 18(19):5705–5711 (1990); Patanjali et al., *Proc. Natl. Acad. U.S.A.* 88:1943–1947 (1991); U.S. Pat. Nos. 5,482,685 and 5,637,685; and Soares et al., *Proc. Natl. Acad. Sci. USA* 91:9228–9232 (1994).

Subtracted cDNA libraries are another means to increase the proportion of less abundant cDNA species. See, Foote et al. in, *Plant Molecular Biology: A Laboratory Manual,* Clark, Ed., Springer-Verlag, Berlin (1997); Kho and Zarbl, *Technique* 3(2):58–63 (1991); Sive and St. John, *Nucl. Acids Res.* 16(22):10937 (1988); *Current Protocols in Molecular Biology,* Ausubel et al., Eds., Greene Publishing and Wiley-lnterscience, New York (1995); and, Swaroop et al., *Nucl. Acids Res.* 19)8):1954 (1991). cDNA subtraction kits are commercially available. See, e.g., PCR-Select (Clontech).

To construct genomic libraries, large segments of genomic DNA are generated by random fragmentation. Examples of appropriate molecular biological techniques and instructions are found in Sambrook, et al., *Molecular Cloning: A Laboratory Manual,* 2nd Ed., Cold Spring Harbor Laboratory Vols. 1–3 (1989), Methods in Enzymology, Vol. 152: *Guide to Molecular Cloning Techniques,* Berger and Kimmel, Eds., San Diego: Academic Press, Inc. (1987), *Current Protocols in Molecular Biology,* Ausubel et al., Eds., Greene Publishing and Wiley-lnterscience, New York (1995); *Plant Molecular Biology: A Laboratory Manual,* Clark, Ed., Springer-Verlag, Berlin (1997). Kits for construction of genomic libraries are also commercially available.

The cDNA or genomic library can be screened using a probe based upon the sequence of a nucleic acid of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent. The degree of stringency can be controlled by temperature, ionic strength, pH and the presence of a partially denaturing solvent such as formamide.

Typically, stringent hybridization conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

Exemplary low stringency conditions include hybridization with a buffer solution of 30 to 35% formamide, 1 M NaCl, 1% SDS (sodium dodecyl sulfate) at 37° C., and a wash in 1X to 2X SSC (20X SSC=3.0 M NaCl/0.3 M trisodium citrate) at 50° C. Exemplary moderate stringency conditions include hybridization in 40 to 45% formamide, 1 M NaCl, 1% SDS at 37° C., and a wash in 0.5X to 1X SSC at 55° C. Exemplary high stringency conditions include hybridization in 50% formamide, 1 M NaCl, 1% SDS at 37° C., and a wash in 0.1X SSC at 60° C.

An extensive guide to the hybridization of nucleic acids is found in Tijssen, *Laboratory Techniques in Biochemistry and Molecular Biology— Hybridization with Nucleic Acid Probes,* Part I, Chapter 2 "Overview of principles of hybridization and the strategy of nucleic acid probe assays", Elsevier, New York (1993); and *Current Protocols in Molecular Biology,* Chapter 2, Ausubel et al., Eds., Greene Publishing and Wiley-lnterscience, New York (1995). Often, cDNA libraries will be normalized to increase the representation of relatively rare cDNAs.

The nucleic acids of the invention can be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Examples of techniques useful for in vitro amplification methods are found in Berger, Sambrook, and Ausubel, as well as Mullis et al., U.S. Pat. No. 4,683,202 (1987); and, *PCR Protocols A Guide to Methods and Applications,* Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

PCR-based screening methods have also been described. Wilfinger et al. describe a PCR-based method in which the longest cDNA is identified in the first step so that incomplete clones can be eliminated from study. *BioTechniques,* 22(3): 481–486 (1997).

The isolated nucleic acids of the present invention can also be prepared by direct chemical synthesis by methods such as the phosphotriester method of Narang et al., *Meth. Enzymol.* 68:90–99 (1979); the phosphodiester method of Brown et al., *Meth. Enzymol.* 68:109–151 (1979); the diethylphosphoramidite method of Beaucage et al., *Tetra. Lett.* 22:1859–1862 (1981); the solid phase phosphoramidite triester method described by Beaucage and Caruthers, *Tetra. Letts.* 22(20):1859–1862 (1981), e.g., using an automated synthesizer, e.g., as described in Needham-VanDevanter et al., *Nucleic Acids Res.* 12:6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

The glucans of the present invention are preferably produced in transgenic maize, potato, sugar beet, cassava, sweet potato, rye, barley, wheat, sorghum, oats, millet, triticale, sugarcane and rice. More preferably, the present glucans are produced in maize, potato, sugar beet, sugarcane, cassava, and sweet potato. Even more preferably, the present glucans are produced in maize, sugar beet and potato. Most preferably, the present glucans are produced in maize.

The production of the present glucans in transgenic plants is performed according to methods of transformation that are well known in the art, and thus constitute no part of this invention. The compounds of the present invention are synthesized by insertion of an expression cassette containing a synthetic gene which, when transcribed and translated, yields a GTF enzyme that produces the desired glucans. Such empty expression cassettes, providing appropriate regulatory sequences for plant expression of the desired sequence, are also well-known, and the nucleotide sequence for the gene, either RNA or DNA, can readily be derived from the amino acid sequence for the protein using standard texts and the references provided. The above-mentioned genes preferably employ plant-preferred codons to enhance expression of the desired protein.

The following description further exemplifies the compositions of this invention and the methods of making and using them. However, it will be understood that other methods, known by those of ordinary skill in the art to be equivalent, can also be employed.

The genes that encode for the present enzymes can be inserted into an appropriate expression cassette and introduced into cells of a plant species. Thus, an especially preferred embodiment of this method involves inserting into the genome of the plant a DNA sequence coding for a mutant or wild type enzyme in proper reading frame, together with transcription promoter and initiator sequences active in the plant. Transcription and translation of the DNA sequence under control of the regulatory sequences causes expression of the protein sequence at levels that provide an elevated amount of the protein in the tissues of the plant.

By the term "vector" herein is meant a DNA sequence which is able to replicate and express a foreign gene in a host cell. Typically, the vector has one or more restriction endonuclease recognition sites which may be cut in a predictable fashion by use of the appropriate enzyme such vectors are preferably constructed to include additional structural gene sequences imparting antibiotic or herbicide resistance, which then serve as markers to identify and separate transformed cells. Preferred markers/selection agents include kanamycin, chlorosulfuron, phosphonothricin, hygromycin and methotrexate. A cell in which the foreign genetic material in a vector is functionally expressed has been "transformed" by the vector and is referred to as a "transformant".

A particularly preferred vector is a plasmid, by which is meant a circular double-stranded DNA molecule which is not a part of the chromosomes of the cell.

As mentioned above, both genomic DNA and cDNA encoding the gene of interest may be used in this invention. The gene of interest may also be constructed partially from a cDNA clone and partially from a genomic clone. When the gene of interest has been isolated, genetic constructs are made which contain the necessary regulatory sequences to provide for efficient expression of the gene in the host cell. According to this invention, the genetic construct will contain (a) a genetic sequence coding for the protein or trait of interest and (b) one or more regulatory sequences operably linked on either side of the structural gene of interest. Typically, the regulatory sequences will be selected from the group comprising of promoters and terminators. The regulatory sequences may be from autologous or heterologous sources.

Expression Cassettes

In another embodiment expression cassettes comprising isolated nucleic acids of the present invention are provided. An expression cassette will typically comprise a polynucleotide of the present invention operably linked to transcriptional initiation regulatory sequences which will direct the transcription of the polynucleotide in the intended host cell, such as tissues of a transformed plant.

The construction of such expression cassettes which can be employed in conjunction with the present invention is well known to those of skill in the art in light of the present disclosure. See, e.g., Sambrook et al.; *Molecular Cloning: A Laboratory Manual;* Cold Spring Harbor, New York; (1989); Gelvin et al.; *Plant Molecular Biology Manual* (1990); *Plant Biotechnology: Commercial Prospects and Problems,* eds. Prakash et al.; Oxford & IBH Publishing Co.; New Delhi, India; (1993); and Heslot et al.; *Molecular Biology and Genetic Engineering of Yeasts;* CRC Press, Inc., USA; (1992); each incorporated herein in its entirety by reference.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

Constitutive, tissue-preferred or inducible promoters can be employed. Examples of constitutive promoters include the cauliflower mosaic virus (CaMV) 35S transcription initiation region, the 1'- or 2'- promoter derived from T-DNA of Agrobacterium tumefaciens, the ubiquitin 1 promoter, the actin promoter, the Smas promoter, the cinnamyl alcohol dehydrogenase promoter (U.S. Pat. No. 5,683,439), the Nos promoter, the pEmu promoter, the rubisco promoter, the GRP1–8 promoter, and other transcription initiation regions from various plant genes known to those of skill.

Examples of inducible promoters are the Adhl promoter which is inducible by hypoxia or cold stress, the Hsp70 promoter which is inducible by heat stress, the PPDK promoter which is inducible by light, the ln2 promoter which is safener induced, the ERE promoter which is estrogen induced and the Pepcarboxylase promoter which is light induced.

Examples of promoters under developmental control include promoters that initiate transcription preferentially in certain tissues, such as leaves, roots, fruit, seeds, or flowers. Exemplary promoters for the maize transformation vectors, of the instant invention include any promoter whose expression is specific and limited to endosperm cells. Included are those encoding either 22 kDa zein, opaque2, gamma zein and waxy. Examples of seed-preferred promoters include, but are not limited to, gamma zein promoter and waxy promoter, Boronat,A., Martinez, M. C., Reina, M., Puigdomenech, P. and Palau, J.; Isolation and sequencing of a 28 kDa glutelin-2 gene from maize: Common elements in the 5' flanking regions among zein and glutelin genes; *Plant Sci.* 47:95–102 (1986) and Reina, M., Ponte, I., Guillen, P., Boronat, A. and Palau, J., Sequence analysis of a genomic clone encoding a Zc2 protein from *Zea mays* W64 A, *Nucleic Acids Res.* 18(21):6426 (1990). See the following citation relating to the waxy promoter: Kloesgen, R. B., Gierl, A., Schwarz-Sommer, ZS. and Saedler, H., Molecular analysis of the waxy locus of Zea mays, *Mol. Gen. Genet.* 203:237–244 (1986). An anther specific promoter is 5126 (U.S. Pat. Nos. 5,689,049 and 5,689,051). The disclosures of each of these are incorporated herein by reference in their entirety.

Either heterologous or non-heterologous (i.e., endogenous) promoters can be employed to direct expression of the nucleic acids of the present invention. These promoters can also be used, for example, in expression cassettes to drive expression of sense or antisense nucleic acids to reduce, increase, or alter concentration and/or composition of the proteins of the present invention in a desired tissue. A promoter may be operably linked to the gtf gene, which is followed by the endogenous terminator or the heterogeneous PINII terminator.

The GTF B, GTF C or GTF D protein is directed to the maize endosperm amyloplast using a suitable transit sequence. Transit sequences useful in directing the enzyme into the amyloplast for accumulation within the amyloplast include but are not limited to ribulose biphosphate carboxylase small subunit, waxy, brittle-1, and chlorophyll AB binding protein. The transit sequences are juxtaposed between the promoter and the gtfb, gtfc or gtfd coding sequence and fused in translational reading frame with the gtfb, gtfc or gtfd moiety.

Transit sequences useful in directing the enzyme into the vacuole for accumulation within the vacuole are well known in the art. For vacuolar targeting, see e.g. Ebskamp et al., "Accumulation of Fructose Polymers in Transgenic Tobacco," *Bio/technology;* Vol.12; pp.272–275; (1994); incorporated herein in its entirety by reference.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates. See for example Buchman and Berg, *Mol. Cell Biol.* 8:4395–4405 (1988); Callis et al., *Genes Dev.* 1:1 183–1200 (1987). Use of maize introns Adh1-S intron 1, 2, and 6, the Bronze-1 intron are known in the art. See generally, *The Maize Handbook,* Chapter 116, Freeling and Walbot, Eds., Springer, New York (1994).

The vector comprising the sequences from a polynucleotide of the present invention will typically comprise a marker gene that confers a selectable phenotype on plant cells. Usually, the selectable marker gene will encode antibiotic or herbicide resistance. Suitable genes include those coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance.

Suitable genes coding for resistance to herbicides include those which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), those which act to inhibit action of glutamine synthase, such as phosphinothricin or basta (e.g., the bar gene), or other such genes known in the art. The bar gene encodes resistance to the herbicide basta and the ALS gene encodes resistance to the herbicide chlorosulfuron.

Typical vectors useful for expression of genes in higher plants are well known in the art and include vectors derived from the tumor-inducing (Ti) plasmid of *Agrobacterium tumefaciens* described by Rogers et al., Meth. In Enzymol. 153:253–277 (1987). Exemplary *A. tumefaciens* vectors useful herein are plasmids pKYLX6 and pKYLX7 of Schardl et al., Gene, 61:1–11 (1987) and Berger et al., *Proc. Natl. Acad. Sci. USA* 86:8402–8406 (1989). Another useful vector herein is plasmid pBI101.2 that is available from Clontech Laboratories, Inc. (Palo Alto, Calif.).

A variety of plant viruses that can be employed as vectors are known in the art and include cauliflower mosaic virus (CaMV), geminivirus, brome mosaic virus, and tobacco mosaic virus.

A polynucleotide of the present invention can be expressed in either sense or anti-sense orientation as desired. In plant cells, it has been shown that antisense RNA inhibits gene expression by preventing the accumulation of mRNA which encodes the enzyme of interest, see, e.g., Sheehy et al., *Proc. Natl. Acad. Sci. USA* 85:8805–8809 (1988); and Hiatt et al., U.S. Pat. No. 4,801,340.

Another method of suppression is sense suppression. Introduction of nucleic acid configured in the sense orientation has been shown to be an effective means mRNA accumulation of target genes. For an example of the use of this method to modulate expression of endogenous genes see, Napoli et al., *The Plant Cell* 2:279–289 (1990) and U.S. Pat. No. 5,034,323.

Catalytic RNA molecules or ribozymes can also be used to inhibit expression of plant genes. The inclusion of ribozyme sequences within antisense RNAs confers RNA-cleaving activity upon them, thereby increasing the activity of the constructs. The design and use of target RNA-specific ribozymes is described in Haseloff et al., *Nature* 334:585–591 (1988).

A variety of cross-linking agents, alkylating agents and radical generating species as pendant groups on polynucleotides of the present invention can be used to bind, label, detect, and/or cleave nucleic acids. For example, Vlassov, V. V. et al., *Nucleic Acids Res* (1986) 14:4065–4076, describe covalent bonding of a single-stranded DNA fragment with alkylating derivatives of nucleotides complementary to target sequences. A report of similar work by the same group is that by Knorre, D. G. et al., *Biochimie* (1985) 67:785–789. Iverson and Dervan also showed sequence-specific cleavage of single-stranded DNA mediated by incorporation of a modified nucleotide which was capable of activating cleavage (*J Am Chem Soc* (1987) 109:1241–1243). Meyer, R. B. et al., *J Am Chem Soc* (1989) 111:8517–8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L. et al., *Biochemistry* (1988) 27:3197–3203. Use of crosslinking in triple-helix forming probes was also disclosed by Home, et al., *J Am Chem Soc* (1990) 112:2435–2437. Use of N4, N4-ethanocytosine as an alkylating agent to crosslink to single-stranded oligonucleotides has also been described by Webb and Matteucci, *J Am Chem Soc* (1986) 108:2764–2765; *Nucleic Acids Res* (1986) 14:7661–7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681,941.

Proteins

Proteins of the present invention include proteins derived from the native protein by deletion (so-called truncation), addition or substitution of one or more amino acids at one or more sites in the native protein. Such variants may result from, for example, genetic polymorphism or from human manipulation. Methods for such manipulations are generally known in the art.

For example, amino acid sequence variants of the polypeptide can be prepared by mutations in the cloned DNA sequence encoding the native protein of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488–492; Kunkel et al. (1987) *Methods Enzymol.* 154:367–382; Sambrook et al. (1989) *Molecular Cloning: A Laboratory Manual* (Cold Spring Harbor, New York); U.S. Pat. No. 4,873,192; and the references cited therein; herein incorporated by reference. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

In constructing variants of the proteins of interest, modifications to the nucleotide sequences encoding the variants will be made such that variants continue to possess the desired activity. Obviously, any mutations made in the DNA encoding the variant protein must not place the sequence out of reading frame and preferably will not create complementary regions that could produce secondary mRNA structure. See EP Patent Application Publication No. 75,444.

The isolated proteins of the present invention include a polypeptide comprising at least 23 contiguous amino acids encoded by any one of the nucleic acids of the present invention, or polypeptides which are conservatively modified variants thereof. The proteins of the present invention or variants thereof can comprise any number of contiguous amino acid residues from a polypeptide of the present invention, wherein that number is selected from the group of integers consisting of from 23 to the number of residues in a full-length polypeptide of the present invention. Optionally, this subsequence of contiguous amino acids is at least 25, 30, 35, or 40 amino acids in length, often at least 50, 60, 70, 80, or 90 amino acids in length.

The present invention includes modifications that can be made to an inventive protein of without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

Typically, an intermediate host cell will be used in the practice of this invention to increase the copy number of the cloning vector. With an increased copy number, the vector containing the gene of interest can be isolated in significant quantities for introduction into the desired plant cells.

Host cells that can be used in the practice of this invention include prokaryotes, including bacterial hosts such as *Eschericia coli, Salmonella typhimurium,* and *Serratia marcescens.* Eukaryotic hosts such as yeast or filamentous fungi may also be used in this invention. Since these hosts are also microorganisms, it will be essential to ensure that plant promoters which do not cause expression of the polypeptide in bacteria are used in the vector.

Commonly used prokaryotic control sequences include such commonly used promoters as the beta lactamase (penicillinase) and lactose (lac) promoter systems (Chang et al., *Nature* 198:1056 (1977)), the tryptophan (trp) promoter system (Goeddel et al., *Nucleic Acids Res.* 8:4057 (1980)) and the lambda derived P L promoter and N-gene ribosome binding site (Shimatake et al., *Nature* 292:128 (1981)). The inclusion of selection markers in DNA vectors transfected in *E. coli* is also useful. Examples of such markers include genes specifying resistance to kanamycin, ampicillin, tetracycline, or chloramphenicol.

The vector is selected to allow introduction into the appropriate host cell. Bacterial vectors are typically of plasmid or phage origin. Expression systems for expressing a protein of the present invention are available using Bacillus sp. and Salmonella (Palva et al., *Gene* 22:229–235 (1983); Mosbach et al., *Nature* 302:543–545 (1983)).

Synthesis of heterologous proteins in yeast is well known. See Sherman, F. et al., *Methods in Yeast Genetics,* Cold Spring Harbor Laboratory (1982). Two widely utilized yeast for production of eukaryotic proteins are *Saccharomyces cerevisiae* and *Pichia pastoris. E. coli* and *P. pastoris* are preferred expression systems. Vectors, strains, and protocols for expression in Saccharomyces and Pichia are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques, enzyme activity assays or radio-immunoassays or other standard immunoassay techniques.

The proteins of the present invention can also be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3–284 in *The Peptides: Analysis, Synthesis, Biology. Vol. 2: Special Methods in Peptide Synthesis, Part A.;* Merrifield et al., *J. Am. Chem. Soc.* 85:2149–2156 (1963), and Stewart et al., *Solid Phase Peptide Synthesis,* 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide)) is known to those of skill.

The proteins of this invention may be purified to substantial purity by standard techniques well known in the art, including detergent solubilization, selective precipitation with such substances as ammonium sulfate, column chromatography, immunopurification methods, and others. See, for instance, R. Scopes, *Protein Purification: Principles and Practice,* Springer-Verlag: New York (1982); Deutscher, *Guide to Protein Purification,* Academic Press (1990). For example, antibodies may be raised to the proteins as described herein. Purification from *E. coli* can be achieved following procedures described in U.S. Pat. No. 4,511,503. Detection of the expressed protein is achieved by methods known in the art and include for example, radioimmunoassays, Western blotting techniques enzyme activity assays or immunoprecipitation.

The present invention further provides a method for modulating (i.e., increasing or decreasing) the concentration or composition of the polypeptides of the present invention in a plant or part thereof. Modulation can be effected by increasing or decreasing the concentration and/or the composition (i.e., the ratio of the polypeptides of the present invention) in a plant. The method comprises transforming a plant cell with an expression cassette comprising a polynucleotide of the present invention to obtain a transformed plant cell, growing the transformed plant cell under plant forming conditions, and inducing expression of a polynucleotide of the present invention in the plant for a time sufficient to modulate concentration and/or composition in the plant or plant part.

In some embodiments, the content and/or composition of polypeptides of the present invention in a plant may be modulated by altering, in vivo or in vitro, the promoter of a non-isolated gene of the present invention to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art.

In general, concentration or composition is increased or decreased by at least 5%, 10%, 20%, 30%, 40%, 50%, 60%, 70%, 80%, or 90% relative to a native control plant, plant part, or cell lacking the aforementioned expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds which activate expression from these promoters are well known in the art. In preferred embodiments, the polypeptides of the present invention are modulated in monocots or dicots, preferably maize, sugar beet, potato, cassava, sweet potato, soybeans, sunflower, sorghum, canola, wheat, alfalfa, rice, barley and millet.

Means of detecting the proteins of the present invention are not critical aspects of the present invention. In a preferred embodiment, the proteins are detected and/or quantified using any of a number of well recognized immunological binding assays (see, e.g., U.S. Pat. Nos. 4,366,241; 4,376,110; 4,517,288; and 4,837,168). For a review of the general immunoassays, see also Methods in Cell Biology, Vol. 37: *Antibodies in Cell Biology,* Asai, Ed., Academic Press, Inc. New York (1993); *Basic and Clinical Immunology* 7th Edition, Stites & Terr, Eds. (1991). Moreover, the immunoassays of the present invention can be performed in any of several configurations, e.g., those reviewed in *Enzyme Immunoassay,* Maggio, Ed., CRC Press, Boca Raton, Fla. (1980); Tijan, Practice and Theory of Enzyme Immunoassays, *Laboratory Techniques in Biochemistry and Molecular Biology,* Elsevier Science Publishers B. V., Amsterdam (1985); Harlow and Lane, supra; *Immunoassay: A Practical Guide,* Chan, Ed., Academic Press, Orlando, Fla. (1987); *Principles and Practice of Immunoassays,* Price and Newman Eds., Stockton Press, N.Y. (1991); and *Non-isotopic Immunoassays,* Ngo, Ed., Plenum Press, N.Y. (1988).

Typical methods include Western blot (immunoblot) analysis, analytical biochemical methods such as electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

Non-radioactive labels are often attached by indirect means. Generally, a ligand molecule (e.g., biotin) is covalently bound to the molecule. The ligand then binds to an receptor (e.g., streptavidin) molecule that is either inherently detectable or covalently couples to a signal system, such as a detectable enzyme, a fluorescent compound, or a chemiluminescent compound. A number of ligands and receptors can be used. Where a ligand has a natural receptor, for example, biotin, thyroxine, and cortisol, it can be used in conjunction with the labeled, naturally occurring receptors. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904, which is incorporated herein by reference.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Antibodies can be raised to a protein of the present invention, including individual, allelic, strain, or species variants, and fragments thereof, both in their naturally occurring (full-length) forms and in recombinant forms. Additionally, antibodies are raised to these proteins in either their native configurations or in non-native configurations. Anti-idiotypic antibodies can also be generated. Many methods of making antibodies are known to persons of skill.

In some instances, it is desirable to prepare monoclonal antibodies from various mammalian hosts, such as mice, rodents, primates, humans, etc. Description of techniques for preparing such monoclonal antibodies are found in, e.g., *Basic and Clinical Immunology*, 4th ed., Stites et al., Eds., Lange Medical Publications, Los Altos, Calif., and references cited therein; Harlow and Lane, Supra; Goding, *Monoclonal Antibodies: Principles and Practice,* 2nd ed., Academic Press, New York, N.Y. (1986); and Kohler and Milstein, *Nature* 256:495–497 (1975).

Other suitable techniques involve selection of libraries of recombinant antibodies in phage or similar vectors (see, e.g., Huse et al., *Science* 246:1275–1281 (1989); and Ward et al., *Nature* 341:544–546 (1989); and Vaughan et al., *Nature Biotechnology*, 14:309–314 (1996)). Alternatively, high avidity human monoclonal antibodies can be obtained from transgenic mice comprising fragments of the unrearranged human heavy and light chain Ig loci (i.e., minilocus transgenic mice). Fishwild et al., *Nature Biotech.*, 14:845–851 (1996). Also, recombinant immunoglobulins may be produced. See, Cabilly, U.S. Pat. No. 4,816,567; and Queen et al., *Proc. Nat'l Acad. Sci.* 86:10029–10033 (1989).

Frequently, the proteins and antibodies of the present invention will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like.

Transfection/Transformation of Cells

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method that provides for efficient transformation/transfection may be employed.

A DNA sequence coding for the desired polynucleotide of the present invention, for example a cDNA or a genomic sequence encoding a full length protein, will be used to construct an expression cassette which can be introduced into the desired plant. Isolated nucleic acid acids of the present invention can be introduced into plants according techniques known in the art. Generally, expression cassettes as described above and suitable for transformation of plant cells are prepared.

Techniques for transforming a wide variety of higher plant species are well known and described in the technical, scientific, and patent literature. See, for example, Weising et al., *Ann. Rev. Genet.* 22:421–477 (1988). For example, the DNA construct may be introduced directly into the genomic DNA of the plant cell using techniques such as particle bombardment, silicon fiber delivery, or microinjection of plant cell protoplasts or embryogenic callus. See, e.g., Tomes, et al., Direct DNA Transfer into Intact Plant Cells Via Microprojectile Bombardment. pp.197–213 in Plant Cell, Tissue and Organ Culture, Fundamental Methods. eds. L. Gamborg and G. C. Phillips. Springer-Verlag Berlin Heidelberg New York, 1995. U.S. Pat. No. 5,008,200 Ranch et al. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616.

*Agrobacterium tumefaciens*—meditated transformation techniques are well described in the scientific literature. See, for example Horsch et al., *Science* 233:496–498 (1984), and Fraley et al., *Proc. Natl. Acad. Sci.* 80:4803 (1983). For instance, Agrobacterium transformation of maize is described in U.S. Pat. No. 5,550,318 and WO98/32326 which is incorporated by reference.

Other methods of transfection or transformation include (1) *Agrobacterium rhizogenes*—mediated transformation (see, e.g., Lichtenstein and Fuller In: Genetic Engineering, Vol. 6, PWJ Rigby, Ed., London, Academic Press, 1987; and Lichtenstein, C. P., and Draper, J,. In: DNA Cloning, Vol. II, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16, (2) liposome-mediated DNA uptake (see, e.g., Freeman et al., Plant Cell Physiol. 25:1353, (1984)), (3) the vortexing method (see, e.g., Kindle, *Proc. NatL. Acad. Sci. USA* 87:1228, (1990)).

DNA can also be introduced into plants by direct DNA transfer into pollen as described by Zhou et al., Methods in Enzymology, 101:433 (1983); D. Hess, Intern Rev. Cytol., 107:367 (1987); Luo et al., Plant Mol. Biol. Reporter, 6:165 (1988). Expression of polypeptide coding genes can be obtained by injection of the DNA into reproductive organs of a plant as described by Pena et al., Nature, 325: 274 (1987). DNA can also be injected directly into the cells of immature embryos and the rehydration of desiccated embryos as described by Neuhaus et al., Theor. Appl. Genet., 75:30 (1987); and Benbrook et al., in Proceedings Bio Expo 1986, Butterworth, Stoneham, Mass., pp.27–54 (1986).

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

Transgenic Plant Regeneration

Transformed plant cells which are derived by any of the above transformation techniques can be cultured to regenerate a whole plant which possesses the transformed genotype. Such regeneration techniques may rely on manipulation of certain phytohormones in a tissue culture growth medium, and on a biocide and/or herbicide marker which has been introduced together with a polynucleotide of the present invention. For transformation and regeneration of maize see, Gordon-Kamm et al., *The Plant Cell,* 2:603–618 (1990).

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture,* Macmillan Publishing Company, New York, pp.124–176 (1983); and Binding, *Regeneration of Plants, Plant Protoplasts,* CRC Press, Boca Raton, pp. 21–73 (1985).

The regeneration of plants containing the foreign gene introduced by Agrobacterium can be achieved as described by Horsch et al., *Science,* 227:1229–1231 (1985) and Fraley et al., *Proc. Natl. Acad. Sci. U.S.A.* 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.* 38:467–486 (1987). The regeneration of plants from either single plant protoplasts or various explants is well known in the art. See, for example, Methods for Plant Molecular Biology, A. Weissbach and H. Weissbach, eds., Academic Press, Inc., San Diego, Calif. (1988). For maize cell culture and regeneration see generally, *The Maize Handbook*, Freeling and Walbot, Eds., Springer, New York (1994); *Corn and Corn Improvement,* $3^{rd}$ edition, Sprague and Dudley Eds., American Society of Agronomy, Madison, Wis. (1988).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenic plants is made and new varieties are obtained and propagated vegetatively for commercial use. In seed propagated crops, mature transgenic plants can be self-pollinated to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing a selectable marker can be screened for transmission of the nucleic acid of the present invention by, for example, standard DNA detection techniques. Transgenic lines are also typically evaluated based levels of expression of the heterologous nucleic acid. Expression at the RNA level can be determined initially to identify and quantitate expression-positive plants. Standard techniques for RNA analysis can be employed and include RTPCR amplification assays using oligonucleotide primers designed to amplify only the heterologous RNA templates and solution hybridization assays using heterologous nucleic acid-specific probes. The RNA-positive plants can then be analyzed for protein accumulation by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are screened for the incorporated nucleic acid to identify and select plants with the most appropriate expression profiles.

A preferred embodiment is a transgenic plant that is homozygous for the added heterologous nucleic acid; i.e., a transgenic plant that contains the gene sequence in question at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for copy number of the polynucleotide of the present invention relative to a control plant (i.e., native, non-transgenic). Back-crossing to a parental plant and out-crossing with a non- transgenic plant are also within the scope of the application.

Plants that can be used in the method of the invention include monocotyledonous and dicotyledonous plants. Preferred plants include maize, wheat, rice, barley, oats, sorghum, millet, rye, soybean, sunflower, alfalfa, canola, cotton, potato, sugar beet, cassava, sweet potato, triticale, sugarcane, and transgenic plants thereof.

Seeds derived from plants regenerated from transformed plant cells, plant parts or plant tissues, or progeny derived from the regenerated transformed plants, may be used directly as feed or food, or further processing may occur.

The expression cassette comprising the structural gene for a mutant of this invention operably linked to the desired control sequences can be ligated into a suitable cloning vector. In general, plasmid or viral (bacteriophage) vectors containing replication and control sequences derived from species compatible with the host cell are used. The cloning vector will typically carry a replication origin, as well as specific genes that are capable of providing phenotypic selection markers in transformed host cells. Typically, genes conferring resistance to antibiotics or selected herbicides are used. After the genetic material is introduced into the target cells, successfully transformed cells and/or colonies of cells can be isolated by selection on the basis of these markers.

Typically, an intermediate host cell will be used in the practice of this invention to increase the copy number of the cloning vector. With an increased copy number, the vector containing the gene of interest can be isolated in significant quantities for introduction into the desired plant cells. Host cells that can be used in the practice of this invention include prokaryotes, including bacterial hosts such as *E. coli, S. typhimurium,* and *Serratia marcescens.* Eukaryotic hosts such as yeast or filamentous fungi may also be used in this invention. Since these hosts are also microorganisms, it is preferable to ensure that plant promoters which do not cause expression of the protein in bacteria are used in the vector.

The isolated cloning vector will then be introduced into the plant cell using any convenient technique, including bombardment, transformation using Agrobacterium, electroporation (in protoplasts), retroviruses and microinjection into plant cells. Accordingly, a highly preferred embodiment of the present invention is a transformed maize, sugar beet or potato plant, the cells of which contain as foreign DNA at least one copy of the DNA sequence of an expression cassette of the GTF B, GTF C or GTF D protein.

For example, the potato plant can be transformed via *Agrobacterium tumefaciens* to produce the present glucans. The transformation cassette comprises a patatin promoter, followed by the gtfb, gtfc or gtfd coding sequence and the neomycin phosphotransferase polyadenylation site/terminator. See e.g. Utsumi et al., "Expression and Accumulation for Normal and Modified Soybean Glycinins in Potato Tubers," *Plant Science;* Vol. 102(2); pp.181–188; (1994); (Limerick); incorporated herein in its entirety by reference. The transgenic cassette is placed into a transformation vector. For example, BIN19, or derivatives thereof, are useful when transforming via *Agrobacterium tumefaciens.* See e.g. Visser et al., "Transformation of Homozygous Diploid Potato with an *Agrobacterium-tumefaciens* Binary Vector System by Adventitious Shoot Regeneration on Leaf and Stem Segments," *Plant Mol. Biol.;* Vol. 12(3); pp. 329–338; (1989); incorporated herein in its entirety by reference.

For maize transformation and regeneration see e.g. Armstrong, C., (1994), "Regeneration of Plants from Somatic Cell Cultures: Applications for in vitro Genetic Manipulation," *The Maize Handbook,* Freeling et al. eds, pp. 663–671; incorporated herein in its entirety by reference.

Regenerated putative transgenic plants can be analyzed through PCR and Southern blot analysis using the GTF B, GTF C or GTF D gene as a probe or as template for primers. Northern analysis or RT-PCR can also be performed using RNA isolated from endosperm PCR Protocols: A Guide to Methods and Applications. Academic Press (1990) pp 23–26. MA Innis; DH Gelfand; JJ Sninsky; TJ White eds. B. A. Larkins, R. A. Jones and C. Y. Tsai (1976). Isolation and in vitro translation of zein messenger ribonucleic acid. Biochemistry. 15, No. 25: 5506–5511.

Once a given transformed plant is identified, the glucans synthesized can be isolated, by standard methods, known to one skilled in the art. B. A. Larkins, C. E. Bracker and C. Y. Tsai (1976). Storage protein synthesis in maize isolation of zein-synthesizing polyribosomes. Plant Physiology. 57:740–745. B. A. Larkins and C. Y. Tsai (1977). Dissociation of polysome aggregates by protease K1.Plant Physiology. 60:482–485.

The glucans thus obtained in the transgenic plant can be substituted for modified starches and utilized in the sizing and/or coating steps. For formulations useful in the coating step, see e.g. Heiser et al., "Starch Formations," *Starch and Starch Products in Paper Coating;* Kearney et al., eds., pp. 147–162; (1990); Tappi Press; incorporated herein in its entirety by reference.

The present glucans are utilized in an amount of from about 4 to about 15 weight percent, more preferably from about 5 to about 12 weight percent, also preferably from about 6 to about 8 weight percent. Weight percent is defined as grams of molecule per 100 ml coating solution.

The present glucans are used to replace the starch and/or latex molecules completely, or a starch-glucan or a latex-glucan mixture is used in the slurry. In the coating application, the glucan:starch ratio preferably ranges from about 10:90 to about 100:0; more preferably from about 40:60 to about 100:0; more preferably still from about 60:40 to about 100:0; most preferably about 100:0. The glucan-:latex ratio preferably ranges from about 10:90 to about 100:0; more preferably from about 40:60 to about 100:0; more preferably still from about 60:40 to about 100:0; most preferably about 100:0.

All publications cited in this application are herein incorporated by reference to the same extent as if each individual publication or patent application was specifically and individually indicated to be incorporated by reference.

The present invention will be further described by reference to the following detailed examples. It is understood, however, that there are many extensions, variations, and modifications on the basic theme of the present invention beyond that shown in the examples and description, which are within the spirit and scope of the present invention.

EXAMPLES

Example 1

Construction of gtf expression vectors

The transgene containing the gtf coding sequence was cloned into a plant expression vector. The gamma zein promoter and terminator flanked the coding sequence so as to produce a gtf polypeptide.

Example 2

Transformation

Immature maize embryos were transformed with the gtf expression vectors described above using standard maize particle bombardment and Agrobacterium- mediated transformation methods as described. Plants were regenerated using standard techniques.

Neither T0 nor T1 plants exhibited any deleterious effects upon their health that were significantly different from any other plant derived from regeneration from tissue culture. Seed set was normal and plant height and overall health was normal.

Example 3

Southern Blot Analysis

Southern blots on DNA isolated from transgenic T2 seed from T1 plants were performed essentially by the method described in "Molecular Cloning" Eds. J, Sambrook, E. F. Fritsch and T. Maniatis, Cold Spring Harbor Laboratory Press, 1989. The Plant Transcription Unit (PTU) Analysis and Integration Analysis were performed by probing Southern blots of DNA digested to display the intact PTU. Or in the case of integration analysis, blots were digested with enzymes with recognition sites not present at the ends of the PTU to demonstrate unique integration patterns.

These results demonstrate that the DNA containing the gtf gene was stably integrated into the maize genome of GS3 and that each independent transformation event exhibited at least one gtf transcriptional unit. Southern blots of T2 seed from T1 plants demonstrate the presence of at least eight independent stable transformation events in GS3 for gtfc.

DNA containing the gtfc gene was stably integrated into the maize genome of the same transgenic GS3 events described above. Furthermore, unique DNA integration patterns indicate that each event is derived independently. Southern blots of T2 seed from T1 plant show at least seven independent stable transformation events in GS3 for gtfc.

Example 4

RT-PCR Reverse Transcriptase Polymerase Chain Reaction

RT-PCR was performed by the method described in PCR Protocols: A Guide to Methods and Applications. Academic Press (1990) pp 23–26. MA Innis; DH Gelfand; JJ Sninsky; TJ White eds. The following method was used to isolate mRNA:

Dissected embryo from the seed and discarded embryo;

Pooled the 10 seeds and pulverized the kernel to flour;

Weighed 50-mg kernel meal per sample and 50-mg GS3 kernel meal;

Resuspended each in 300-μl 50 mM MOPS, pH 7.0 by vortexing;

Added to each sample 100-μl α-amylase solution (770 units/mg, heat stable, prepared by dissolving 1.0 mg in 1.4-ml 50 mM MOPS, pH 7.0);

Carried out the digestion in a 85° C. water bath for 1 h with periodic vortexing;

Added to the reaction 1.2-ml methanol, kept at −20° C. for 10 min, and centrifuged in at 15K for 10 min;

Decanted and washed the pellet with 1.0-ml 70% methanol;

Reverse Transcriptase PCR (RT-PCR) of mRNA isolated form gtfc transgenic maize was performed using PCR primers near the 5' end and within the gtfc coding sequence were used on mRNA isolated from GS3, T2 seed.

The RT-PCR bands indicate expression of the transgene in T2 seed in at least seven independent stable transformation events in GS3 for gtf-c.

Primer pairs include:

position 115–386: ACAGCAACTTCAGCAACATCT-CAAC and GACGGCTGTTTTAATTTACCAATCT position 144–400: CGCCACTGTTACTGATAAT-GTTTCT and CTTGACTAAGTGATGACGGCTGTTT Example 5

Evaluation of Soluble Glucans

Transgenic plants expressing glucosyltransferase were used to isolate soluble glucans. The gtfd glucans produced by mutant N471D were evaluated and the results are shown in the following table.

| EVALUATION OF SOLUBLE GLUCANS | | |
|---|---|---|
| Starch I.D. | N471D (2%) | Pen Gum 280 (9%) |
| Rod Number | 9 | 7 | 9 |
| Starch Pick-up (#/3300 sq. ft.) | 1.04 | 2.01 | 2.51 |
| HST (sec.) | 1.1 | 1.9 | 2.3 |
| G. Stiffness CD | 65 | 75 | 64 |
| MD | 135 | 135 | 143 |
| IGT Pick v.v.p. | 110 | 187 | 193 |
| G. Porosity cc. | 30 | 17 | 12 |

*HST is a size test, the larger the number the more sizing the paper gets.
*IGT pick is a test for paper surface strength, the higher the number the better.
*G. porosity is a test for the porosity of the paper. The lower the number the tighter the paper, it also means the better the film formed by the starch.

Example 6 gtfb and gtfd mutants

Gtfb and gtfd mutants were generated by site directed mutagenesis as well known in the art. The nomenclature used to identify the mutant enzymes used to produce the present glucans is described above.

Site-directed mutagenesis of gtfb resulted in mutant GTF B enzymes having changes at positions I448V; D457N; D567T; K1014T; D457N/D567T; D457N/D571K; D567T/D571K; D567T/D571K/K1014T; I448V/D457N/D567T/D571K/K779Q/K1014T; Y169A/Y170A/Y171A; K779Q; K1014T and D567T/D571K/K1014T.

Site-directed mutagenesis of gtfd resulted in mutant GTF D enzymes having changes at positions T589D; T589E; N471D; N471D/T589D; and N471D/T589E.

All publications cited in this application are indicative of the level of skill of those skilled in the art to which this invention pertains. All publications are herein incorporated by reference to the same extent as if each individual publication or patent application was specifically and individually indicated to be incorporated by reference.

Variations on the above embodiments are within the ability of one of ordinary skill in the art, and such variations do not depart from the scope of the present invention as described in the following claims.

What is claimed is:

1. An isolated nucleic acid comprising a member selected from the group consisting of:

(a) a polynucleotide which encodes a glucosyltransferase B polypeptide having changes at positions selected from the group consisting of I448V; D457N; D567T; K1014T; D457N/D567T; D457N/D571K; D567T/D571K; D567T/D571K/K1014T; I448V/D457N/D567T/D571K/K779Q/K1014T; Y169A/Y170A/Y171A; and K779Q;

(b) a polynucleotide which encodes a glucosyltransferase D polypeptide having changes at positions selected from the group consisting of T589D; T589E; N471D; N471D/T589D; and N471D/T589E;

(c) a polynucleotide complementary to a polynucleotide of (a) or (b).

2. An expression cassette comprising at least one gtfb or gtfd nucleic acid operably linked to a promoter.

3. The expression cassette of claim 2, wherein the promoter is the 22 Kda zein opaque 2, gamma zein or waxy.

4. A vector comprising an expression cassette of claim 2.

5. A host cell introduced with at least one expression cassette of claim 2.

6. The host cell of claim 5 that is a plant cell.

7. A transgenic plant comprising at least one expression cassette of claim 2.

8. The plant of claim 7, wherein the plant is maize, potato, sugar beet, cassava or sweet potato.

9. The plant of claim 8 which is maize.

10. The plant of claim 9 which is deficient in starch biosynthesis.

11. The plant of claim 10 which is selected from the group consisting of sh-2, bt-1 and bt-2.

12. A seed or tuber from the plant of claim 7.

13. The seed or tuber of claim 12 that is from maize, sugar beet, potato, cassava or sweet potato.

14. A method for producing a glucan in a plant comprising:

(a) transforming a plant cell with the expression cassette of claim 2;

(b) growing the plant cell under plant growing conditions to produce a regenerated plant; and (d) inducing expression of the polynucleotide for a time sufficient to produce the glucan in the regenerated plant.

15. The method of claim 14 wherein the plant is maize, sugar beet, potato, cassava or sweet potato.

16. The method of claim 15 wherein the plant is a maize plant deficient in starch biosynthesis.

17. The method of claim 16 wherein the plant is sh-2, bt-1 or bt-2.

18. The method of claim 14 wherein the promoter is selected from the group consisting of 22 kDa zein, opaque 2, gamma zein and waxy.

19. The method of claim 14 wherein the expression cassette contains a transit sequence selected from the group consisting of ribulose biphosphate carboxylase small subunit, waxy, brittle-1 and chlorophyll AB binding protein to produce a transgenic plant.

20. The method of claim 14 wherein the glucan is produced in the amyloplast or vacuole of the plant cell.

21. The method of claim 20 wherein the glucan is produced in the amyloplast of potato or the vacuole of sugar beet.

22. An isolated protein comprising a member selected from the group consisting of:

(a) a polypeptide encoded by a gtfb nucleic acid having changes at positions selected from the group consisting of; I448V; D457N; D567T; K1014T; D457N/D567T; D457N/D571K; D567T/D571K; D567T/D571K/K1014T; I448V/D457N/D567T/D571K/K779Q/K1014T; Y169A/Y170A/Y171A; and K779Q; and (b) a polypeptide encoded by a gtfd nucleic acid having changes at positions selected from the group consisting of T589D; T589E; N471D; N471D/T589D; and N471D/T589E.

23. A glucan produced by the protein of claim 22.

24. A ribonucleic acid sequence encoding a protein of claim 22.

25. A transgenic plant comprising at least one protein of claim 22.

26. A paper sizing and/or coating composition comprising a glucan produced in a plant transformed with a gene encoding a glucosyltransferase B or D enzyme, wild type or mutant, a starch, a latex, a thermoplastic molecule or combinations thereof.

27. The composition of claim 26 comprising 4–15% weight percent of said glucan.

28. The composition of claim 27, wherein said glucan is 5–12% weight percent.

29. The composition of claim 26 wherein the combination of one or more of glucan: starch, glucan:latex and glucan:thermoplastic molecule is in a ratio from about 10:90 to about 100:0.

30. The composition of claim 29, wherein said ratio is about 40:60 to about 100:0.

31. The composition of claim 30, wherein said ratio is about 100:0.

32. A paper comprising the glucan of claim 26.

33. A paper sizing and/or coating composition comprising glucan and starch wherein the glucan is produced in the amyloplast and/or vacuole of a maize line deficient in starch biosynthesis, transformed with a gene encoding a glucosyltransferase B or D enzyme, wild type or mutant.

34. A paper comprising the glucan of claim 33.

* * * * *

SEQUENCE LISTING

<160> NUMBER OF SEQ ID NOS: 6

<210> SEQ ID NO 1
<211> LENGTH: 4460
<212> TYPE: DNA
<213> ORGANISM: streptococcus mutans
<220> FEATURE:
<221> NAME/KEY: CDS
<222> LOCATION: (9)...(4434)

<400> SEQUENCE: 1

```
ggttccta atg gac aag aaa gtg cgt tat aaa ctg cgc aaa gtt aaa aaa         50
         Met Asp Lys Lys Val Arg Tyr Lys Leu Arg Lys Val Lys Lys
          1               5                  10 aga tgg gtg aca gta tct gtt gca tct gct gtg atg act tta act aca         98
Arg Trp Val Thr Val Ser Val Ala Ser Ala Val Met Thr Leu Thr Thr
 15                  20                  25                  30 ctt tcg ggt ggc ttg gtt aaa gca gat tct aat gaa tcg aaa tcc caa        146
Leu Ser Gly Gly Leu Val Lys Ala Asp Ser Asn Glu Ser Lys Ser Gln
                 35                  40                  45 att tct aat gat tct aat acc agt gtt gtt act gct aat gaa gaa tct        194
Ile Ser Asn Asp Ser Asn Thr Ser Val Val Thr Ala Asn Glu Glu Ser
             50                  55                  60 aat gta ata acc gaa gcg aca tct aag caa gaa gct gct agt agt caa        242
Asn Val Ile Thr Glu Ala Thr Ser Lys Gln Glu Ala Ala Ser Ser Gln
 65                  70                  75 act aat cat aca gta acg aca agc agt agc tct act tcg gta gtt aat        290
Thr Asn His Thr Val Thr Thr Ser Ser Ser Ser Thr Ser Val Val Asn
                 80                  85                  90 ccc aaa gag gtt gta agt aat cct tat act gtt ggg gaa aca gct tct        338
Pro Lys Glu Val Val Ser Asn Pro Tyr Thr Val Gly Glu Thr Ala Ser
 95                 100                 105                 110 aat ggt gaa aag ctt caa aat caa aca act aca gtt gac aaa act tct        386
Asn Gly Glu Lys Leu Gln Asn Gln Thr Thr Thr Val Asp Lys Thr Ser
                115                 120                 125 gaa gct gct gct aat aat att agt aaa caa aca acc gaa gct gat aca        434
Glu Ala Ala Ala Asn Asn Ile Ser Lys Gln Thr Thr Glu Ala Asp Thr
            130                 135                 140 gat gtt att gat gat agc aat gca gcc aat cta caa ata ttg gaa aaa        482
Asp Val Ile Asp Asp Ser Asn Ala Ala Asn Leu Gln Ile Leu Glu Lys
            145                 150                 155 ctt ccc aat gta aaa gaa att gat ggt aag tat tat tat gac aat        530
Leu Pro Asn Val Lys Glu Ile Asp Gly Lys Tyr Tyr Tyr Tyr Asp Asn
160                 165                 170 aac ggc aaa gtt cgt act aat ttt aca tta att gct gat ggc aaa att        578
Asn Gly Lys Val Arg Thr Asn Phe Thr Leu Ile Ala Asp Gly Lys Ile
175                 180                 185                 190 tta cat ttt gat gaa act ggc tat act gat aca tca att gac act        626
Leu His Phe Asp Glu Thr Gly Ala Tyr Thr Asp Thr Ser Ile Asp Thr
                195                 200                 205 gta aat aaa gat atc gtc aca aca aga agt aat cta tac aaa aaa tat        674
Val Asn Lys Asp Ile Val Thr Thr Arg Ser Asn Leu Tyr Lys Lys Tyr
            210                 215                 220 aat caa gtt tat gat cgc tct gca cag agc ttt gag cat gtt gat cat        722
Asn Gln Val Tyr Asp Arg Ser Ala Gln Ser Phe Glu His Val Asp His
            225                 230                 235 tat ttg aca gct gag agt tgg tat cgt cct aag tac atc ttg aag gat        770
Tyr Leu Thr Ala Glu Ser Trp Tyr Arg Pro Lys Tyr Ile Leu Lys Asp
            240                 245                 250
```

-continued

| | |
|---|---|
| ggc aaa aca tgg aca cag tca aca gaa aaa gat ttc cgt ccc tta ttg<br>Gly Lys Thr Trp Thr Gln Ser Thr Glu Lys Asp Phe Arg Pro Leu Leu<br>255                      260                          265                      270 | 818 |
| atg aca tgg tgg cct gac caa gaa acg cag cgt caa tat gtt aac tac<br>Met Thr Trp Trp Pro Asp Gln Glu Thr Gln Arg Gln Tyr Val Asn Tyr<br>                  275                          280                        285 | 866 |
| atg aat gca cag ctt ggc att aac aag act tat gat gat aca agt aat<br>Met Asn Ala Gln Leu Gly Ile Asn Lys Thr Tyr Asp Asp Thr Ser Asn<br>             290                          295                        300 | 914 |
| caa ttg caa tta aat att gca gct gca act att caa gca aaa att gag<br>Gln Leu Gln Leu Asn Ile Ala Ala Ala Thr Ile Gln Ala Lys Ile Glu<br>        305                      310                        315 | 962 |
| gcc aaa att aca act tta aag aat act gat tgg ctg cgt cag act att<br>Ala Lys Ile Thr Thr Leu Lys Asn Thr Asp Trp Leu Arg Gln Thr Ile<br>320                      325                          330 | 1010 |
| tcc gca ttt gtt aag aca cag tca gct tgg aac agt gac agc gaa aaa<br>Ser Ala Phe Val Lys Thr Gln Ser Ala Trp Asn Ser Asp Ser Glu Lys<br>335                      340                        345                      350 | 1058 |
| ccg ttt gat gat cat tta caa aat gga gca gtg ctt tac gat aat gaa<br>Pro Phe Asp Asp His Leu Gln Asn Gly Ala Val Leu Tyr Asp Asn Glu<br>                  355                          360                        365 | 1106 |
| gga aaa tta acg cct tat gct aat tcc aac tac cgt atc tta aat cgc<br>Gly Lys Leu Thr Pro Tyr Ala Asn Ser Asn Tyr Arg Ile Leu Asn Arg<br>             370                          375                        380 | 1154 |
| acc ccg acc aat caa acc gga aag aaa gat cca agg tat aca gct gat<br>Thr Pro Thr Asn Gln Thr Gly Lys Lys Asp Pro Arg Tyr Thr Ala Asp<br>        385                      390                        395 | 1202 |
| aac act atc ggc ggt tat gaa ttc ctt ttg gcc aac gat gtg gat aat<br>Asn Thr Ile Gly Gly Tyr Glu Phe Leu Leu Ala Asn Asp Val Asp Asn<br>400                      405                          410 | 1250 |
| tct aat cct gtc gtg cag gcc gaa caa ttg aac tgg cta cat ttt ctc<br>Ser Asn Pro Val Val Gln Ala Glu Gln Leu Asn Trp Leu His Phe Leu<br>415                      420                        425                      430 | 1298 |
| atg aac ttt ggt aac att tat gcc aat gat ccg gat gct aac ttt gat<br>Met Asn Phe Gly Asn Ile Tyr Ala Asn Asp Pro Asp Ala Asn Phe Asp<br>                  435                          440                        445 | 1346 |
| tcc att cgt gtt gat gcg gta gat aat gtg gat gct gac ttg ctc caa<br>Ser Ile Arg Val Asp Ala Val Asp Asn Val Asp Ala Asp Leu Leu Gln<br>             450                          455                        460 | 1394 |
| att gct ggg gat tac ctc aaa gct gct aag ggg atc cat aaa aat gat<br>Ile Ala Gly Asp Tyr Leu Lys Ala Ala Lys Gly Ile His Lys Asn Asp<br>        465                      470                        475 | 1442 |
| aag gct gct aat gat cat ttg tct att tta gag gca tgg agt gac aac<br>Lys Ala Ala Asn Asp His Leu Ser Ile Leu Glu Ala Trp Ser Asp Asn<br>480                      485                        490 | 1490 |
| gac act cct tac ctt cat gat gat ggc gac aat atg att aat atg gac<br>Asp Thr Pro Tyr Leu His Asp Asp Gly Asp Asn Met Ile Asn Met Asp<br>495                      500                        505                      510 | 1538 |
| aat aag ctg cgt ttg tct cta tta ttt tca tta gct aaa ccc tta aat<br>Asn Lys Leu Arg Leu Ser Leu Leu Phe Ser Leu Ala Lys Pro Leu Asn<br>             515                          520                        525 | 1586 |
| caa cgt tca ggc atg aat cct ctg atc act aac agt ttg gtg aat cgt<br>Gln Arg Ser Gly Met Asn Pro Leu Ile Thr Asn Ser Leu Val Asn Arg<br>        530                      535                        540 | 1634 |
| act gat gat aat gct gaa act gcc gca gtc cct tct tat tcc ttc atc<br>Thr Asp Asp Asn Ala Glu Thr Ala Ala Val Pro Ser Tyr Ser Phe Ile<br>545                      550                        555 | 1682 |
| cgt gcc cat gac agt gaa gtg cag gat ttg att gct gat atc atc aag<br>Arg Ala His Asp Ser Glu Val Gln Asp Leu Ile Ala Asp Ile Ile Lys<br>        560                      565                        570 | 1730 |

```
gca gaa atc aat cct aat gtt gtc ggg tat tca ttc act atg gag gaa    1778
Ala Glu Ile Asn Pro Asn Val Val Gly Tyr Ser Phe Thr Met Glu Glu
575             580             585             590 atc aag aag gct ttc gag att tac aac aaa gac tta tta gct aca gag    1826
Ile Lys Lys Ala Phe Glu Ile Tyr Asn Lys Asp Leu Leu Ala Thr Glu
            595             600             605 aag aaa tac aca cac tat aat acg gca ctt tct tat gcc ctg ctt tta    1874
Lys Lys Tyr Thr His Tyr Asn Thr Ala Leu Ser Tyr Ala Leu Leu Leu
        610             615             620 acc aac aaa tcc agt gtg ccg cgt gtc tat tat ggg gat atg ttt aca    1922
Thr Asn Lys Ser Ser Val Pro Arg Val Tyr Tyr Gly Asp Met Phe Thr
    625             630             635 gat gac ggg caa tac atg gct cat aag acg atc aat tac gaa gcc atc    1970
Asp Asp Gly Gln Tyr Met Ala His Lys Thr Ile Asn Tyr Glu Ala Ile
640             645             650 gaa acc ctg ctt aaa gct cgt att aag tat gtt tca ggc ggt caa gcc    2018
Glu Thr Leu Leu Lys Ala Arg Ile Lys Tyr Val Ser Gly Gly Gln Ala
655             660             665             670 atg cgc aat caa cag gtt ggc aat tct gaa atc att acg tct gtc cgc    2066
Met Arg Asn Gln Gln Val Gly Asn Ser Glu Ile Ile Thr Ser Val Arg
            675             680             685 tat ggt aaa ggt gct ttg aaa gca acg gat aca ggg gac cgc acc aca    2114
Tyr Gly Lys Gly Ala Leu Lys Ala Thr Asp Thr Gly Asp Arg Thr Thr
        690             695             700 cgg act tca gga gtg gcc gtg att gaa ggc aat aac cct tct tta cgt    2162
Arg Thr Ser Gly Val Ala Val Ile Glu Gly Asn Asn Pro Ser Leu Arg
    705             710             715 ttg aag gct tct gat cgc gtg gtt gtc aat atg gga gca gcc cat aag    2210
Leu Lys Ala Ser Asp Arg Val Val Val Asn Met Gly Ala Ala His Lys
720             725             730 aac caa gct tac cga cct tta ctc ttg acc aca gat aac ggt atc aag    2258
Asn Gln Ala Tyr Arg Pro Leu Leu Leu Thr Thr Asp Asn Gly Ile Lys
735             740             745             750 gct tat cat tcc gat caa gaa gcg gct ggt ttg gtg cgc tac acc aat    2306
Ala Tyr His Ser Asp Gln Glu Ala Ala Gly Leu Val Arg Tyr Thr Asn
            755             760             765 gac aga ggg gaa ttg atc ttc aca gcg gct gat att aaa ggc tat gcc    2354
Asp Arg Gly Glu Leu Ile Phe Thr Ala Ala Asp Ile Lys Gly Tyr Ala
        770             775             780 aac cct caa gtt tct ggc tat tta ggt gtc tgg gtt cca gta ggc gct    2402
Asn Pro Gln Val Ser Gly Tyr Leu Gly Val Trp Val Pro Val Gly Ala
    785             790             795 gcg ctg atc aag atg ttc gcg ttg cgg cta gca cgg ccc cat caa cag    2450
Ala Leu Ile Lys Met Phe Ala Leu Arg Leu Ala Arg Pro His Gln Gln
800             805             810 atg gca agt gtg cat caa aat gcg gcc ctt gat tca cgc gtc atg ttt    2498
Met Ala Ser Val His Gln Asn Ala Ala Leu Asp Ser Arg Val Met Phe
815             820             825             830 gaa ggt ttc tct aat ttc caa gct ttc gcc act aaa aaa gag gaa tat    2546
Glu Gly Phe Ser Asn Phe Gln Ala Phe Ala Thr Lys Lys Glu Glu Tyr
            835             840             845 acc aat gtt gtg att gct aag aat gtg gat aag ttt gcg gaa tgg ggg    2594
Thr Asn Val Val Ile Ala Lys Asn Val Asp Lys Phe Ala Glu Trp Gly
        850             855             860 gtc aca gac ttt gaa atg gca ccg cag tat gtg tct tca acg gat ggt    2642
Val Thr Asp Phe Glu Met Ala Pro Gln Tyr Val Ser Ser Thr Asp Gly
    865             870             875 tct ttc ttg gat tct gtg atc caa aac ggc tat gct ttt acg gac cgt    2690
Ser Phe Leu Asp Ser Val Ile Gln Asn Gly Tyr Ala Phe Thr Asp Arg
```

-continued

|     |     |     |      |
|-----|-----|-----|------|
| 880 | 885 | 890 |      |

```
tat gat ttg gga att tcc aaa cct aat aaa tac ggg aca gcc gat gat     2738
Tyr Asp Leu Gly Ile Ser Lys Pro Asn Lys Tyr Gly Thr Ala Asp Asp
895             900             905             910 ttg gtg aaa gcc atc aaa gcg tta cac agc aag ggc att aag gta atg     2786
Leu Val Lys Ala Ile Lys Ala Leu His Ser Lys Gly Ile Lys Val Met
            915             920             925 gct gac tgg gtg cct gat caa atg tat gct ttc cct gaa aaa gaa gtg     2834
Ala Asp Trp Val Pro Asp Gln Met Tyr Ala Phe Pro Glu Lys Glu Val
        930             935             940 gta act gca acc cgt gtt gat aag tat ggg act cct gtt gca gga agt     2882
Val Thr Ala Thr Arg Val Asp Lys Tyr Gly Thr Pro Val Ala Gly Ser
    945             950             955 cag atc aaa aac acc ctt tat gta gtt gat ggt aag agt tct ggt aaa     2930
Gln Ile Lys Asn Thr Leu Tyr Val Val Asp Gly Lys Ser Ser Gly Lys
960             965             970 gat caa caa gcc aag tat ggg gga gct ttc tta gag gag ctg caa gcg     2978
Asp Gln Gln Ala Lys Tyr Gly Gly Ala Phe Leu Glu Glu Leu Gln Ala
975             980             985             990 aag tat ccg gag ctt ttt gcg aga aaa caa att tcc aca ggg gtt ccg     3026
Lys Tyr Pro Glu Leu Phe Ala Arg Lys Gln Ile Ser Thr Gly Val Pro
            995             1000            1005 atg gat cct tct gtt aag att aag caa tgg tct gcc aag tac ttt aat     3074
Met Asp Pro Ser Val Lys Ile Lys Gln Trp Ser Ala Lys Tyr Phe Asn
        1010            1015            1020 ggg aca aat att tta ggg cgc gga gca ggc tat gtc tta aaa gat cag     3122
Gly Thr Asn Ile Leu Gly Arg Gly Ala Gly Tyr Val Leu Lys Asp Gln
    1025            1030            1035 gca act aat act tac ttt aat att tca gat aat aaa gaa ata aac ttc     3170
Ala Thr Asn Thr Tyr Phe Asn Ile Ser Asp Asn Lys Glu Ile Asn Phe
1040            1045            1050 ctt cct aaa aca ttg tta aac caa gat agt caa gtt ggt ttc tct tat     3218
Leu Pro Lys Thr Leu Leu Asn Gln Asp Ser Gln Val Gly Phe Ser Tyr
1055            1060            1065            1070 gac ggt aaa ggt tat gtt tat tat tca acg agt ggt tac caa gcc aaa     3266
Asp Gly Lys Gly Tyr Val Tyr Tyr Ser Thr Ser Gly Tyr Gln Ala Lys
            1075            1080            1085 aat act ttc atc agc gaa ggt gat aaa tgg tat tat ttt gat aat aac     3314
Asn Thr Phe Ile Ser Glu Gly Asp Lys Trp Tyr Tyr Phe Asp Asn Asn
        1090            1095            1100 ggt tat atg gtc act ggt gct caa tca att aac ggt gtt aat tat tat     3362
Gly Tyr Met Val Thr Gly Ala Gln Ser Ile Asn Gly Val Asn Tyr Tyr
    1105            1110            1115 ttc tta tca aat ggc cta cag ctc aga gat gct att ctt aag aat gaa     3410
Phe Leu Ser Asn Gly Leu Gln Leu Arg Asp Ala Ile Leu Lys Asn Glu
1120            1125            1130 gat gga act tac gct tat tat gga aat gac ggt cgc cgt tat gaa aat     3458
Asp Gly Thr Tyr Ala Tyr Tyr Gly Asn Asp Gly Arg Arg Tyr Glu Asn
1135            1140            1145            1150 ggt tat tat caa ttc atg agt ggt gta tgg cgt cac ttc aat aat ggt     3506
Gly Tyr Tyr Gln Phe Met Ser Gly Val Trp Arg His Phe Asn Asn Gly
            1155            1160            1165 gaa atg agt gtt gga tta act gta att gat ggt cag gtt caa tac ttt     3554
Glu Met Ser Val Gly Leu Thr Val Ile Asp Gly Gln Val Gln Tyr Phe
        1170            1175            1180 gat gaa atg ggc tat caa gcc aaa gga aaa ttt gta aca act gcc gat     3602
Asp Glu Met Gly Tyr Gln Ala Lys Gly Lys Phe Val Thr Thr Ala Asp
    1185            1190            1195 ggt aaa ata aga tat ttt gat aag caa tct ggg aac atg tac cgt aat     3650
```

```
Gly Lys Ile Arg Tyr Phe Asp Lys Gln Ser Gly Asn Met Tyr Arg Asn
       1200                1205                1210 cgt ttt att gaa aac gaa gaa ggt aaa tgg ctg tat ctc ggt gaa gat      3698
Arg Phe Ile Glu Asn Glu Glu Gly Lys Trp Leu Tyr Leu Gly Glu Asp
1215                1220                1225                1230 ggt gca gca gtg aca gga tct caa acc att aac ggt caa cac ctg tac      3746
Gly Ala Ala Val Thr Gly Ser Gln Thr Ile Asn Gly Gln His Leu Tyr
                1235                1240                1245 ttt aga gca aac ggt gtt cag gtc aag ggt gaa ttt gtc act gac cac      3794
Phe Arg Ala Asn Gly Val Gln Val Lys Gly Glu Phe Val Thr Asp His
        1250                1255                1260 cac ggc cgt atc agc tat tac gac ggc aat tca ggg gat caa atc cgc      3842
His Gly Arg Ile Ser Tyr Tyr Asp Gly Asn Ser Gly Asp Gln Ile Arg
    1265                1270                1275 aac cgc ttt gtc cgc aat gct cag ggt caa tgg ttc tac ttt gat aac      3890
Asn Arg Phe Val Arg Asn Ala Gln Gly Gln Trp Phe Tyr Phe Asp Asn
1280                1285                1290 aat ggc tat gcc gta acc ggt gcc aga acc att aac ggt caa ctc cta      3938
Asn Gly Tyr Ala Val Thr Gly Ala Arg Thr Ile Asn Gly Gln Leu Leu
1295                1300                1305                1310 tac ttt aga gca aac ggt gtt cag gtc aag ggt gaa ttt gtc act gac      3986
Tyr Phe Arg Ala Asn Gly Val Gln Val Lys Gly Glu Phe Val Thr Asp
                1315                1320                1325 cgc tac ggc cgt atc agc tat tac gac ggc aat tca ggg gat caa atc      4034
Arg Tyr Gly Arg Ile Ser Tyr Tyr Asp Gly Asn Ser Gly Asp Gln Ile
        1330                1335                1340 cgc aac cgc ttt gtc cgc aat gct cag ggt caa tgg ttc tac ttt gat      4082
Arg Asn Arg Phe Val Arg Asn Ala Gln Gly Gln Trp Phe Tyr Phe Asp
    1345                1350                1355 aac aat ggc tat gcc gta acc ggt gcc aga acc att aac ggt caa cac      4130
Asn Asn Gly Tyr Ala Val Thr Gly Ala Arg Thr Ile Asn Gly Gln His
1360                1365                1370 cta tac ttt aga gca aac ggt gtt cag gtc aag ggt gaa ttt gtc act      4178
Leu Tyr Phe Arg Ala Asn Gly Val Gln Val Lys Gly Glu Phe Val Thr
1375                1380                1385                1390 gac cgc cac ggc cgt atc agc tat tac gac ggc aat tca ggg gat caa      4226
Asp Arg His Gly Arg Ile Ser Tyr Tyr Asp Gly Asn Ser Gly Asp Gln
                1395                1400                1405 atc cgc aac cgc ttt gtc cgc aat gct cag ggt caa tgg ttc tac ttt      4274
Ile Arg Asn Arg Phe Val Arg Asn Ala Gln Gly Gln Trp Phe Tyr Phe
        1410                1415                1420 gat aac aat ggc tat gcc gta acc ggt gcc aga acc att aac ggt caa      4322
Asp Asn Asn Gly Tyr Ala Val Thr Gly Ala Arg Thr Ile Asn Gly Gln
    1425                1430                1435 cac cta tac ttt aga gca aac ggt gtt cag gtc aag ggt gaa ttt gtc      4370
His Leu Tyr Phe Arg Ala Asn Gly Val Gln Val Lys Gly Glu Phe Val
1440                1445                1450 act gac cgc tac ggc cgt atc agt tat tac gat gct aac tct gga gaa      4418
Thr Asp Arg Tyr Gly Arg Ile Ser Tyr Tyr Asp Ala Asn Ser Gly Glu
1455                1460                1465                1470 cga gtt cgg att aac t aattgttttt tcgctctctt aagtta                    4460
Arg Val Arg Ile Asn
            1475

<210> SEQ ID NO 2
<211> LENGTH: 1475
<212> TYPE: PRT
<213> ORGANISM: Streptococcus mutans

<400> SEQUENCE: 2
```

-continued

```
Met Asp Lys Lys Val Arg Tyr Lys Leu Arg Lys Val Lys Lys Arg Trp
 1               5                  10                  15

Val Thr Val Ser Val Ala Ser Ala Val Met Thr Leu Thr Thr Leu Ser
             20                  25                  30

Gly Gly Leu Val Lys Ala Asp Ser Asn Glu Ser Lys Ser Gln Ile Ser
         35                  40                  45

Asn Asp Ser Asn Thr Ser Val Val Thr Ala Asn Glu Glu Ser Asn Val
 50                  55                  60

Ile Thr Glu Ala Thr Ser Lys Gln Glu Ala Ala Ser Ser Gln Thr Asn
 65                  70                  75                  80

His Thr Val Thr Thr Ser Ser Ser Thr Ser Val Val Asn Pro Lys
                 85                  90                  95

Glu Val Val Ser Asn Pro Tyr Thr Val Gly Thr Ala Ser Asn Gly
                100                 105                 110

Glu Lys Leu Gln Asn Gln Thr Thr Thr Val Asp Lys Thr Ser Glu Ala
         115                 120                 125

Ala Ala Asn Asn Ile Ser Lys Gln Thr Thr Glu Ala Asp Thr Asp Val
     130                 135                 140

Ile Asp Asp Ser Asn Ala Ala Asn Leu Gln Ile Leu Glu Lys Leu Pro
145                 150                 155                 160

Asn Val Lys Glu Ile Asp Gly Lys Tyr Tyr Tyr Tyr Asp Asn Asn Gly
                165                 170                 175

Lys Val Arg Thr Asn Phe Thr Leu Ile Ala Asp Gly Lys Ile Leu His
                180                 185                 190

Phe Asp Glu Thr Gly Ala Tyr Thr Asp Thr Ser Ile Asp Thr Val Asn
             195                 200                 205

Lys Asp Ile Val Thr Thr Arg Ser Asn Leu Tyr Lys Lys Tyr Asn Gln
     210                 215                 220

Val Tyr Asp Arg Ser Ala Gln Ser Phe Glu His Val Asp His Tyr Leu
225                 230                 235                 240

Thr Ala Glu Ser Trp Tyr Arg Pro Lys Tyr Ile Leu Lys Asp Gly Lys
                245                 250                 255

Thr Trp Thr Gln Ser Thr Glu Lys Asp Phe Arg Pro Leu Leu Met Thr
                260                 265                 270

Trp Trp Pro Asp Gln Glu Thr Gln Arg Gln Tyr Val Asn Tyr Met Asn
         275                 280                 285

Ala Gln Leu Gly Ile Asn Lys Thr Tyr Asp Asp Thr Ser Asn Gln Leu
     290                 295                 300

Gln Leu Asn Ile Ala Ala Ala Thr Ile Gln Ala Lys Ile Glu Ala Lys
305                 310                 315                 320

Ile Thr Thr Leu Lys Asn Thr Asp Trp Leu Arg Gln Thr Ile Ser Ala
                325                 330                 335

Phe Val Lys Thr Gln Ser Ala Trp Asn Ser Asp Ser Glu Lys Pro Phe
                340                 345                 350

Asp Asp His Leu Gln Asn Gly Ala Val Leu Tyr Asp Asn Glu Gly Lys
         355                 360                 365

Leu Thr Pro Tyr Ala Asn Ser Asn Tyr Arg Ile Leu Asn Arg Thr Pro
     370                 375                 380

Thr Asn Gln Thr Gly Lys Lys Asp Pro Arg Tyr Thr Ala Asp Asn Thr
385                 390                 395                 400

Ile Gly Gly Tyr Glu Phe Leu Leu Ala Asn Asp Val Asp Asn Ser Asn
                405                 410                 415

Pro Val Val Gln Ala Glu Gln Leu Asn Trp Leu His Phe Leu Met Asn
```

-continued

```
                420                 425                 430
Phe Gly Asn Ile Tyr Ala Asn Asp Pro Asp Ala Asn Phe Asp Ser Ile
            435                 440                 445

Arg Val Asp Ala Val Asp Asn Val Asp Ala Asp Leu Leu Gln Ile Ala
450                 455                 460

Gly Asp Tyr Leu Lys Ala Ala Lys Gly Ile His Lys Asn Asp Lys Ala
465                 470                 475                 480

Ala Asn Asp His Leu Ser Ile Leu Glu Ala Trp Ser Asp Asn Asp Thr
            485                 490                 495

Pro Tyr Leu His Asp Asp Gly Asp Asn Met Ile Asn Met Asp Asn Lys
            500                 505                 510

Leu Arg Leu Ser Leu Leu Phe Ser Leu Ala Lys Pro Leu Asn Gln Arg
        515                 520                 525

Ser Gly Met Asn Pro Leu Ile Thr Asn Ser Leu Val Asn Arg Thr Asp
    530                 535                 540

Asp Asn Ala Glu Thr Ala Ala Val Pro Ser Tyr Ser Phe Ile Arg Ala
545                 550                 555                 560

His Asp Ser Glu Val Gln Asp Leu Ile Ala Asp Ile Ile Lys Ala Glu
            565                 570                 575

Ile Asn Pro Asn Val Val Gly Tyr Ser Phe Thr Met Glu Glu Ile Lys
            580                 585                 590

Lys Ala Phe Glu Ile Tyr Asn Lys Asp Leu Leu Ala Thr Glu Lys Lys
        595                 600                 605

Tyr Thr His Tyr Asn Thr Ala Leu Ser Tyr Ala Leu Leu Leu Thr Asn
    610                 615                 620

Lys Ser Val Pro Arg Val Tyr Tyr Gly Asp Met Phe Thr Asp Asp
625                 630                 635                 640

Gly Gln Tyr Met Ala His Lys Thr Ile Asn Tyr Glu Ala Ile Glu Thr
            645                 650                 655

Leu Leu Lys Ala Arg Ile Lys Tyr Val Ser Gly Gln Ala Met Arg
        660                 665                 670

Asn Gln Gln Val Gly Asn Ser Glu Ile Ile Thr Ser Val Arg Tyr Gly
            675                 680                 685

Lys Gly Ala Leu Lys Ala Thr Asp Thr Gly Asp Arg Thr Thr Arg Thr
        690                 695                 700

Ser Gly Val Ala Val Ile Glu Gly Asn Asn Pro Ser Leu Arg Leu Lys
705                 710                 715                 720

Ala Ser Asp Arg Val Val Asn Met Gly Ala Ala His Lys Asn Gln
            725                 730                 735

Ala Tyr Arg Pro Leu Leu Leu Thr Thr Asp Asn Gly Ile Lys Ala Tyr
            740                 745                 750

His Ser Asp Gln Glu Ala Ala Gly Leu Val Arg Tyr Thr Asn Asp Arg
        755                 760                 765

Gly Glu Leu Ile Phe Thr Ala Ala Asp Ile Lys Gly Tyr Ala Asn Pro
    770                 775                 780

Gln Val Ser Gly Tyr Leu Gly Val Trp Val Pro Val Gly Ala Ala Leu
785                 790                 795                 800

Ile Lys Met Phe Ala Leu Arg Leu Ala Arg Pro His Gln Gln Met Ala
            805                 810                 815

Ser Val His Gln Asn Ala Ala Leu Asp Ser Arg Val Met Phe Glu Gly
            820                 825                 830

Phe Ser Asn Phe Gln Ala Phe Ala Thr Lys Lys Glu Glu Tyr Thr Asn
        835                 840                 845
```

-continued

```
Val Val Ile Ala Lys Asn Val Asp Lys Phe Ala Glu Trp Gly Val Thr
850                 855                 860

Asp Phe Glu Met Ala Pro Gln Tyr Val Ser Ser Thr Asp Gly Ser Phe
865                 870                 875                 880

Leu Asp Ser Val Ile Gln Asn Gly Tyr Ala Phe Thr Asp Arg Tyr Asp
                885                 890                 895

Leu Gly Ile Ser Lys Pro Asn Lys Tyr Gly Thr Ala Asp Asp Leu Val
                900                 905                 910

Lys Ala Ile Lys Ala Leu His Ser Lys Gly Ile Lys Val Met Ala Asp
                915                 920                 925

Trp Val Pro Asp Gln Met Tyr Ala Phe Pro Glu Lys Glu Val Val Thr
            930                 935                 940

Ala Thr Arg Val Asp Lys Tyr Gly Thr Pro Val Ala Gly Ser Gln Ile
945                 950                 955                 960

Lys Asn Thr Leu Tyr Val Val Asp Gly Lys Ser Ser Gly Lys Asp Gln
                965                 970                 975

Gln Ala Lys Tyr Gly Gly Ala Phe Leu Glu Glu Leu Gln Ala Lys Tyr
                980                 985                 990

Pro Glu Leu Phe Ala Arg Lys Gln Ile Ser Thr Gly Val Pro Met Asp
            995                 1000                1005

Pro Ser Val Lys Ile Lys Gln Trp Ser Ala Lys Tyr Phe Asn Gly Thr
            1010                1015                1020

Asn Ile Leu Gly Arg Gly Ala Gly Tyr Val Leu Lys Asp Gln Ala Thr
1025                1030                1035                1040

Asn Thr Tyr Phe Asn Ile Ser Asp Asn Lys Glu Ile Asn Phe Leu Pro
                1045                1050                1055

Lys Thr Leu Leu Asn Gln Asp Ser Gln Val Gly Phe Ser Tyr Asp Gly
            1060                1065                1070

Lys Gly Tyr Val Tyr Tyr Ser Thr Ser Gly Tyr Gln Ala Lys Asn Thr
            1075                1080                1085

Phe Ile Ser Glu Gly Asp Lys Trp Tyr Tyr Phe Asp Asn Asn Gly Tyr
            1090                1095                1100

Met Val Thr Gly Ala Gln Ser Ile Asn Gly Val Asn Tyr Tyr Phe Leu
1105                1110                1115                1120

Ser Asn Gly Leu Gln Leu Arg Asp Ala Ile Leu Lys Asn Glu Asp Gly
                1125                1130                1135

Thr Tyr Ala Tyr Tyr Gly Asn Asp Gly Arg Arg Tyr Glu Asn Gly Tyr
            1140                1145                1150

Tyr Gln Phe Met Ser Gly Val Trp Arg His Phe Asn Asn Gly Glu Met
            1155                1160                1165

Ser Val Gly Leu Thr Val Ile Asp Gly Gln Val Gln Tyr Phe Asp Glu
            1170                1175                1180

Met Gly Tyr Gln Ala Lys Gly Lys Phe Val Thr Thr Ala Asp Gly Lys
1185                1190                1195                1200

Ile Arg Tyr Phe Asp Lys Gln Ser Gly Asn Met Tyr Arg Asn Arg Phe
                1205                1210                1215

Ile Glu Asn Glu Glu Gly Lys Trp Leu Tyr Leu Gly Glu Asp Gly Ala
            1220                1225                1230

Ala Val Thr Gly Ser Gln Thr Ile Asn Gly Gln His Leu Tyr Phe Arg
            1235                1240                1245

Ala Asn Gly Val Gln Val Lys Gly Glu Phe Val Thr Asp His His Gly
            1250                1255                1260
```

-continued

```
Arg Ile Ser Tyr Tyr Asp Gly Asn Ser Gly Asp Gln Ile Arg Asn Arg
1265                1270                1275                1280

Phe Val Arg Asn Ala Gln Gly Gln Trp Phe Tyr Phe Asp Asn Asn Gly
                1285                1290                1295

Tyr Ala Val Thr Gly Ala Arg Thr Ile Asn Gly Gln Leu Leu Tyr Phe
            1300                1305                1310

Arg Ala Asn Gly Val Gln Val Lys Gly Glu Phe Val Thr Asp Arg Tyr
        1315                1320                1325

Gly Arg Ile Ser Tyr Tyr Asp Gly Asn Ser Gly Asp Gln Ile Arg Asn
    1330                1335                1340

Arg Phe Val Arg Asn Ala Gln Gly Gln Trp Phe Tyr Phe Asp Asn Asn
1345                1350                1355                1360

Gly Tyr Ala Val Thr Gly Ala Arg Thr Ile Asn Gly Gln His Leu Tyr
                1365                1370                1375

Phe Arg Ala Asn Gly Val Gln Val Lys Gly Glu Phe Val Thr Asp Arg
            1380                1385                1390

His Gly Arg Ile Ser Tyr Tyr Asp Gly Asn Ser Gly Asp Gln Ile Arg
        1395                1400                1405

Asn Arg Phe Val Arg Asn Ala Gln Gly Gln Trp Phe Tyr Phe Asp Asn
    1410                1415                1420

Asn Gly Tyr Ala Val Thr Gly Ala Arg Thr Ile Asn Gly Gln His Leu
1425                1430                1435                1440

Tyr Phe Arg Ala Asn Gly Val Gln Val Lys Gly Glu Phe Val Thr Asp
                1445                1450                1455

Arg Tyr Gly Arg Ile Ser Tyr Tyr Asp Ala Asn Ser Gly Glu Arg Val
            1460                1465                1470

Arg Ile Asn
        1475

<210> SEQ ID NO 3
<211> LENGTH: 4896
<212> TYPE: DNA
<213> ORGANISM: streptococcus mutans
<220> FEATURE:
<221> NAME/KEY: CDS
<222> LOCATION: (199)...(4326)

<400> SEQUENCE: 3 taattgttttt ttcgctctct taagttaatt aagagggcgt ttctagggtt aggagttttta      60 aatattattt attattttttc taaaaaatga agaatttcat tataaattaa ttacgataca     120
ttgtgctttt gttatagaag tgttacaata ctagtgtttt atatcaaaac actaactcta     180
actatttttg gaggaaat atg gaa aag aaa gta cgt ttt aaa tta cgt aaa       231
                   Met Glu Lys Lys Val Arg Phe Lys Leu Arg Lys
                    1               5                   10 gta aag aaa aga tgg gtg aca gta tct att gct tca gct gta gtg act       279
Val Lys Lys Arg Trp Val Thr Val Ser Ile Ala Ser Ala Val Val Thr
                15                  20                  25 ttg acc tct ctt tca gga agt cta gta aaa gca gat tca act gac gac       327
Leu Thr Ser Leu Ser Gly Ser Leu Val Lys Ala Asp Ser Thr Asp Asp
            30                  35                  40 cgt caa cag gcg gtt aca gaa tct cag gct agt ctt gtg acg aca agt       375
Arg Gln Gln Ala Val Thr Glu Ser Gln Ala Ser Leu Val Thr Thr Ser
        45                  50                  55 gaa gca gca aaa gaa act ctg act gct act gat aca agt aca gca act       423
Glu Ala Ala Lys Glu Thr Leu Thr Ala Thr Asp Thr Ser Thr Ala Thr
    60                  65                  70                  75
```

```
tca gca aca tct caa cca acc gcc act gtt act gat aat gtt tct aca       471
Ser Ala Thr Ser Gln Pro Thr Ala Thr Val Thr Asp Asn Val Ser Thr
                80                  85                  90 aca aac cag tct aca aat act act gct aat aca gct aat ttt gtc gtt       519
Thr Asn Gln Ser Thr Asn Thr Thr Ala Asn Thr Ala Asn Phe Val Val
        95                 100                 105 aaa cca aca aca act tcg gaa cag gct aaa act gat aat agt gac aaa       567
Lys Pro Thr Thr Thr Ser Glu Gln Ala Lys Thr Asp Asn Ser Asp Lys
            110                 115                 120 ata att act aca tca aaa gcg gta aac cgt tta act gcg act ggt aaa       615
Ile Ile Thr Thr Ser Lys Ala Val Asn Arg Leu Thr Ala Thr Gly Lys
        125                 130                 135 ttt gtt cct gct aac aat aat act gca cat cca aaa act gtc act gat       663
Phe Val Pro Ala Asn Asn Asn Thr Ala His Pro Lys Thr Val Thr Asp
140                 145                 150                 155 aaa ata gtt cca ata aaa cca aag att ggt aaa tta aaa cag ccg tca       711
Lys Ile Val Pro Ile Lys Pro Lys Ile Gly Lys Leu Lys Gln Pro Ser
                160                 165                 170 tca ctt agt caa gat gat att gca gcc tta ggt aat gtc aaa aat atc       759
Ser Leu Ser Gln Asp Asp Ile Ala Ala Leu Gly Asn Val Lys Asn Ile
            175                 180                 185 aga aaa gtg aac ggt aaa tat tat tat tat aaa gaa gat gga act ctt       807
Arg Lys Val Asn Gly Lys Tyr Tyr Tyr Tyr Lys Glu Asp Gly Thr Leu
        190                 195                 200 caa aag aat tat gct tta aac att aat ggg aaa act ttc ttc ttt gat       855
Gln Lys Asn Tyr Ala Leu Asn Ile Asn Gly Lys Thr Phe Phe Phe Asp
    205                 210                 215 gaa aca gga gca tta tca aat aat act tta cct agt aaa aag ggt aat       903
Glu Thr Gly Ala Leu Ser Asn Asn Thr Leu Pro Ser Lys Lys Gly Asn
220                 225                 230                 235 atc act aat aat gat aac act aac agc ttt gct caa tat aat cag gtc       951
Ile Thr Asn Asn Asp Asn Thr Asn Ser Phe Ala Gln Tyr Asn Gln Val
                240                 245                 250 tat agt aca gat gtt gca aac ttc gaa cat gtt gat cat tat ttg aca       999
Tyr Ser Thr Asp Val Ala Asn Phe Glu His Val Asp His Tyr Leu Thr
            255                 260                 265 gcc gaa agt tgg tat cgt cct aaa tac atc tta aaa gat ggc aaa aca      1047
Ala Glu Ser Trp Tyr Arg Pro Lys Tyr Ile Leu Lys Asp Gly Lys Thr
        270                 275                 280 tgg aca cag tca aca gaa aaa gat ttc cgt ccc tta ctg atg aca tgg      1095
Trp Thr Gln Ser Thr Glu Lys Asp Phe Arg Pro Leu Leu Met Thr Trp
    285                 290                 295 tgg cct gac caa gaa acg cag cgt caa tat gtt aac tac atg aat gca      1143
Trp Pro Asp Gln Glu Thr Gln Arg Gln Tyr Val Asn Tyr Met Asn Ala
300                 305                 310                 315 cag ctt ggt att cat caa aca tac aat aca gca acc agt ccg ctt caa      1191
Gln Leu Gly Ile His Gln Thr Tyr Asn Thr Ala Thr Ser Pro Leu Gln
                320                 325                 330 ttg aat tta gct gct cag aca ata caa act aag atc gaa gaa aaa atc      1239
Leu Asn Leu Ala Ala Gln Thr Ile Gln Thr Lys Ile Glu Glu Lys Ile
            335                 340                 345 act gca gaa aag aat acc aat tgg ctg cgt cag act att tcc gca ttt      1287
Thr Ala Glu Lys Asn Thr Asn Trp Leu Arg Gln Thr Ile Ser Ala Phe
        350                 355                 360 gtt aag aca cag tca gct tgg aac agt gac agc gaa aaa ccg ttt gat      1335
Val Lys Thr Gln Ser Ala Trp Asn Ser Asp Ser Glu Lys Pro Phe Asp
    365                 370                 375 gat cac tta caa aaa ggg gca ttg ctt tac agt aat aat agc aaa cta      1383
Asp His Leu Gln Lys Gly Ala Leu Leu Tyr Ser Asn Asn Ser Lys Leu
380                 385                 390                 395
```

-continued

```
act tca cag gct aat tcc aac tac cgt atc tta aat cgc acc ccg act     1431
Thr Ser Gln Ala Asn Ser Asn Tyr Arg Ile Leu Asn Arg Thr Pro Thr
                    400                 405                 410 aat caa acc gga aag aaa gat cca agg tat aca gct gat cgc acc att     1479
Asn Gln Thr Gly Lys Lys Asp Pro Arg Tyr Thr Ala Asp Arg Thr Ile
                415                 420                 425 ggc ggt tac gaa ttc ttg tta gcc aat gat gtg gat aat tct aat cct     1527
Gly Gly Tyr Glu Phe Leu Leu Ala Asn Asp Val Asp Asn Ser Asn Pro
            430                 435                 440 gtt gtt cag gca gaa cag ctg aac tgg ctc cac ttt ctt atg aac ttt     1575
Val Val Gln Ala Glu Gln Leu Asn Trp Leu His Phe Leu Met Asn Phe
        445                 450                 455 ggt aac att tat gcc aat gat ccg gat gct aac ttt gat tcc att cgt     1623
Gly Asn Ile Tyr Ala Asn Asp Pro Asp Ala Asn Phe Asp Ser Ile Arg
    460                 465                 470                 475 gtt gat gcg gtg gat aat gtg gat gct gac ttg ctc caa att gct ggg     1671
Val Asp Ala Val Asp Asn Val Asp Ala Asp Leu Leu Gln Ile Ala Gly
                480                 485                 490 gat tac ctc aaa gct gct aag ggg atc cat aaa aat gat aag gct gct     1719
Asp Tyr Leu Lys Ala Ala Lys Gly Ile His Lys Asn Asp Lys Ala Ala
            495                 500                 505 aat gat cat ttg tct att tta gag gca tgg agc tat aac gac act cct     1767
Asn Asp His Leu Ser Ile Leu Glu Ala Trp Ser Tyr Asn Asp Thr Pro
        510                 515                 520 tac ctt cat gat gat ggc gac aat atg att aac atg gat aac agg tta     1815
Tyr Leu His Asp Asp Gly Asp Asn Met Ile Asn Met Asp Asn Arg Leu
    525                 530                 535 cgt ctt tcc ttg ctt tat tca tta gct aaa cct ttg aat caa cgt tca     1863
Arg Leu Ser Leu Leu Tyr Ser Leu Ala Lys Pro Leu Asn Gln Arg Ser
540                 545                 550                 555 ggc atg aat cct ctc atc act aac agt ctg gtg aat cga act gat gat     1911
Gly Met Asn Pro Leu Ile Thr Asn Ser Leu Val Asn Arg Thr Asp Asp
                560                 565                 570 aat gct gaa act gcc gca gtc cct tct tat tcc ttc atc cgt gcc cat     1959
Asn Ala Glu Thr Ala Ala Val Pro Ser Tyr Ser Phe Ile Arg Ala His
            575                 580                 585 gac agt gaa gtg cag gac ttg att cgc aat att att aga aca gaa atc     2007
Asp Ser Glu Val Gln Asp Leu Ile Arg Asn Ile Ile Arg Thr Glu Ile
        590                 595                 600 aat cct aat gtt gtc ggg tat tca ttc act acg gag gaa atc aag aag     2055
Asn Pro Asn Val Val Gly Tyr Ser Phe Thr Thr Glu Glu Ile Lys Lys
    605                 610                 615 gct ttc gag att tac aac aaa gac tta tta gct aca gag aag aaa tac     2103
Ala Phe Glu Ile Tyr Asn Lys Asp Leu Leu Ala Thr Glu Lys Lys Tyr
620                 625                 630                 635 aca cac tat aat acg gca ctt tct tat gcc ctg ctt tta acc aac aaa     2151
Thr His Tyr Asn Thr Ala Leu Ser Tyr Ala Leu Leu Leu Thr Asn Lys
                640                 645                 650 tcc agt gtg ccg cgt gtc tat tat ggg gat atg ttt aca gat gac ggg     2199
Ser Ser Val Pro Arg Val Tyr Tyr Gly Asp Met Phe Thr Asp Asp Gly
            655                 660                 665 caa tac atg gct cat aag acg atc aat tac gaa gcc atc gaa acc ctg     2247
Gln Tyr Met Ala His Lys Thr Ile Asn Tyr Glu Ala Ile Glu Thr Leu
        670                 675                 680 ctt aaa gct cgt att aag tat gtt tca ggc ggt caa gcc atg cgc aat     2295
Leu Lys Ala Arg Ile Lys Tyr Val Ser Gly Gly Gln Ala Met Arg Asn
    685                 690                 695 caa cag gtt ggc aat tct gaa atc att acg tct gtc cgc tat ggt aaa     2343
Gln Gln Val Gly Asn Ser Glu Ile Ile Thr Ser Val Arg Tyr Gly Lys
```

```
                    -continued
700              705              710              715 ggt gct ttg aaa gca acg gat aca ggg gac cgc acc aca cgg act tca    2391
Gly Ala Leu Lys Ala Thr Asp Thr Gly Asp Arg Thr Thr Arg Thr Ser
            720              725              730 gga gtg gcc gtg att gaa ggc aat aac cct tct tta cgt ttg aag gct    2439
Gly Val Ala Val Ile Glu Gly Asn Asn Pro Ser Leu Arg Leu Lys Ala
            735              740              745 tct gat cgc gtg gtt gtc aat atg gga gca gcc cat aag aac caa gct    2487
Ser Asp Arg Val Val Val Asn Met Gly Ala Ala His Lys Asn Gln Ala
        750              755              760 tac cga cct tta ctc ttg acc aca gat aac ggt atc aag gct tat cat    2535
Tyr Arg Pro Leu Leu Leu Thr Thr Asp Asn Gly Ile Lys Ala Tyr His
        765              770              775 tcc gat caa gaa gcg gct ggt ttg gtg cgc tac acc aat gac aga ggg    2583
Ser Asp Gln Glu Ala Ala Gly Leu Val Arg Tyr Thr Asn Asp Arg Gly
780              785              790              795 gaa ttg atc ttc aca gcg gct gat att aaa ggc tat gcc aac cct caa    2631
Glu Leu Ile Phe Thr Ala Ala Asp Ile Lys Gly Tyr Ala Asn Pro Gln
            800              805              810 gtt tct ggc tat tta ggt gtc tgg gtt cca gta ggc gct gcc gct gat    2679
Val Ser Gly Tyr Leu Gly Val Trp Val Pro Val Gly Ala Ala Ala Asp
            815              820              825 caa gat gtt cgc gtt gcg gct agc acg gcc cca tca aca gat ggc aag    2727
Gln Asp Val Arg Val Ala Ala Ser Thr Ala Pro Ser Thr Asp Gly Lys
            830              835              840 tct gtg cat caa aat gcg gcc ctt gat tca cgc gtc atg ttt gaa ggt    2775
Ser Val His Gln Asn Ala Ala Leu Asp Ser Arg Val Met Phe Glu Gly
845              850              855 ttc tct aat ttc caa gct ttc gcc act aaa aaa gag gaa tat acc aat    2823
Phe Ser Asn Phe Gln Ala Phe Ala Thr Lys Lys Glu Glu Tyr Thr Asn
860              865              870              875 gtt gtg att gct aag aat gtg gat aag ttt gcg gaa tgg ggg gtc aca    2871
Val Val Ile Ala Lys Asn Val Asp Lys Phe Ala Glu Trp Gly Val Thr
            880              885              890 gac ttt gaa atg gca ccg cag tat gtg tct tca acg gat ggt tct ttc    2919
Asp Phe Glu Met Ala Pro Gln Tyr Val Ser Ser Thr Asp Gly Ser Phe
            895              900              905 ttg gat tct gtg atc caa aac ggc tat gct ttt acg gac cgt tat gat    2967
Leu Asp Ser Val Ile Gln Asn Gly Tyr Ala Phe Thr Asp Arg Tyr Asp
        910              915              920 ttg gga att tcc aaa cct aat aaa tac ggg aca gcc gat gat ttg gtg    3015
Leu Gly Ile Ser Lys Pro Asn Lys Tyr Gly Thr Ala Asp Asp Leu Val
        925              930              935 aaa gcc atc aaa gcg tta cac agc aag ggc att aag gta atg gct gac    3063
Lys Ala Ile Lys Ala Leu His Ser Lys Gly Ile Lys Val Met Ala Asp
940              945              950              955 tgg gtg cct gat caa atg tat gct ctc cct gaa aaa gaa gtg gta act    3111
Trp Val Pro Asp Gln Met Tyr Ala Leu Pro Glu Lys Glu Val Val Thr
            960              965              970 gca acc cgt gtt gat aag tat ggg act cct gtt gca gga agt cag atc    3159
Ala Thr Arg Val Asp Lys Tyr Gly Thr Pro Val Ala Gly Ser Gln Ile
            975              980              985 aaa aac acc ctt tat gta gtt gat ggt aag agt tct ggt aaa gat caa    3207
Lys Asn Thr Leu Tyr Val Val Asp Gly Lys Ser Ser Gly Lys Asp Gln
            990              995              1000 caa gcc aag tat ggg gga gct ttc tta gag gag ctg caa gcg aag tat    3255
Gln Ala Lys Tyr Gly Gly Ala Phe Leu Glu Glu Leu Gln Ala Lys Tyr
    1005             1010             1015 ccg gag ctt ttt gcg aga aaa caa att tcc aca ggg gtt ccg atg gat    3303
```

-continued

```
Pro Glu Leu Phe Ala Arg Lys Gln Ile Ser Thr Gly Val Pro Met Asp
1020                1025                1030                1035 cct tct gtt aag att aag caa tgg tct gcc aag tac ttt aat ggg aca        3351
Pro Ser Val Lys Ile Lys Gln Trp Ser Ala Lys Tyr Phe Asn Gly Thr
            1040                1045                1050 aat att tta ggg cgc gga gca ggc tat gtc tta aaa gat cag gca acc        3399
Asn Ile Leu Gly Arg Gly Ala Gly Tyr Val Leu Lys Asp Gln Ala Thr
        1055                1060                1065 aat act tac ttc agt ctt gtt tca gac aac acc ttc ctt cct aaa tcg        3447
Asn Thr Tyr Phe Ser Leu Val Ser Asp Asn Thr Phe Leu Pro Lys Ser
    1070                1075                1080 tta gtt aac cca aat cac gga aca agc agt tct gta act gga ttg gta        3495
Leu Val Asn Pro Asn His Gly Thr Ser Ser Ser Val Thr Gly Leu Val
1085                1090                1095 ttt gat ggt aaa ggt tat gtt tat tat tca acg agt ggt aac caa gct        3543
Phe Asp Gly Lys Gly Tyr Val Tyr Tyr Ser Thr Ser Gly Asn Gln Ala
1100                1105                1110                1115 aaa aat gct ttc att agc tta gga aat aat tgg tat tat ttc gat aat        3591
Lys Asn Ala Phe Ile Ser Leu Gly Asn Asn Trp Tyr Tyr Phe Asp Asn
            1120                1125                1130 aac ggt tat atg gtc act ggt gct caa tca att aac ggt gct aat tat        3639
Asn Gly Tyr Met Val Thr Gly Ala Gln Ser Ile Asn Gly Ala Asn Tyr
        1135                1140                1145 tat ttc tta tca aat ggt att caa tta aga aat gct att tat gat aat        3687
Tyr Phe Leu Ser Asn Gly Ile Gln Leu Arg Asn Ala Ile Tyr Asp Asn
    1150                1155                1160 ggt aat aaa gta ttg tct tat tat gga aat gat ggc cgt cgt tat gaa        3735
Gly Asn Lys Val Leu Ser Tyr Tyr Gly Asn Asp Gly Arg Arg Tyr Glu
1165                1170                1175 aat ggt tac tat ctc ttt ggt caa caa tgg cgt tat ttc caa aat ggt        3783
Asn Gly Tyr Tyr Leu Phe Gly Gln Gln Trp Arg Tyr Phe Gln Asn Gly
1180                1185                1190                1195 att atg gct gtc ggc tta aca cgt gtt cat ggt gct gtt caa tat ttt        3831
Ile Met Ala Val Gly Leu Thr Arg Val His Gly Ala Val Gln Tyr Phe
            1200                1205                1210 gat gct tct ggg ttc caa gct aaa gga cag ttt att aca act gct gat        3879
Asp Ala Ser Gly Phe Gln Ala Lys Gly Gln Phe Ile Thr Thr Ala Asp
        1215                1220                1225 gga aag ctg cgt tac ttt gat aga gac tca gga aat caa att tca aat        3927
Gly Lys Leu Arg Tyr Phe Asp Arg Asp Ser Gly Asn Gln Ile Ser Asn
    1230                1235                1240 cgt ttt gtt aga aat tcc aag gga gaa tgg ttc tta ttt gat cac aat        3975
Arg Phe Val Arg Asn Ser Lys Gly Glu Trp Phe Leu Phe Asp His Asn
1245                1250                1255 ggt gtc gct gta acc ggt act gta acg ttc aat gga caa cgt ctt tac        4023
Gly Val Ala Val Thr Gly Thr Val Thr Phe Asn Gly Gln Arg Leu Tyr
1260                1265                1270                1275 ttt aaa cct aat ggt gtt caa gcc aaa gga gaa ttt atc aga gat gca        4071
Phe Lys Pro Asn Gly Val Gln Ala Lys Gly Glu Phe Ile Arg Asp Ala
            1280                1285                1290 aat gga tat cta aga tat tat gat cct aat tcc gga aat gaa gtt cgt        4119
Asn Gly Tyr Leu Arg Tyr Tyr Asp Pro Asn Ser Gly Asn Glu Val Arg
        1295                1300                1305 aat cgc ttt gtt aga aat tcc aag gga gaa tgg ttc tta ttt gat cac        4167
Asn Arg Phe Val Arg Asn Ser Lys Gly Glu Trp Phe Leu Phe Asp His
    1310                1315                1320 aat ggt atc gct gta act ggt gcc aga gtt gtt aat gga cac gcc tct        4215
Asn Gly Ile Ala Val Thr Gly Ala Arg Val Val Asn Gly His Ala Ser
1325                1330                1335
```

-continued

```
att tta agt cta atg gtg ttc agg cta agg gag agc tca tta cag agc    4263
Ile Leu Ser Leu Met Val Phe Arg Leu Arg Glu Ser Ser Leu Gln Ser
1340                1345                1350                1355 gta aag gtc gta tca aat act atg atc cta att ccg gaa atg aag ttc    4311
Val Lys Val Val Ser Asn Thr Met Ile Leu Ile Pro Glu Met Lys Phe
                1360                1365                1370 gta atc gtt atg tga gaacatcatc aggaaactgg tactattttg gcaatgatgg    4366
Val Ile Val Met *
            1375 ttatgcctta attggttggc atgttgttga aggaagacgt gtttactttg atgaaaatgg    4426 tatttatcgt tatgccagtc atgatcaaag aaaccactgg gattatgatt acagaagaga    4486 ctttggtcgt ggcagcagca gtgctgttcg ttttagacac cctcgtaatg gattctttga    4546 caatttcttt agatttttaat acttatctta gaagaacagt attttgatta tttcatcttc    4606 taatgttaaa aagaagtctg agctgtaaat ttctcaggct tcttttttgg ctgttatcaa    4666 aaaaaagag ctaaactaaa atattgtttg gcttctatta aattaatgtc aatgcttaca     4726 attttgtaag ctacgattct ttaagtgtaa gatatctttt cttttttat tttaagatag     4786 tagtataaat aaattaagtt ataatgataa aaaggagaag ctatgttttt agaaatcaat    4846 cacttagaaa aagttttcg tacccgtttt tcaaaagaag aaacgcatgc                4896
```

<210> SEQ ID NO 4
<211> LENGTH: 1375
<212> TYPE: PRT
<213> ORGANISM: streptococcus mutans

<400> SEQUENCE: 4

```
Met Glu Lys Lys Val Arg Phe Lys Leu Arg Val Lys Lys Arg Trp
1               5                   10                  15

Val Thr Val Ser Ile Ala Ser Val Val Thr Leu Thr Ser Leu Ser
            20                  25                  30

Gly Ser Leu Val Lys Ala Asp Ser Thr Asp Arg Gln Gln Ala Val
        35                  40                  45

Thr Glu Ser Gln Ala Ser Leu Val Thr Thr Ser Glu Ala Ala Lys Glu
50                  55                  60

Thr Leu Thr Ala Thr Asp Thr Ser Thr Ala Thr Ser Ala Thr Ser Gln
65                  70                  75                  80

Pro Thr Ala Thr Val Thr Asp Asn Val Ser Thr Thr Asn Gln Ser Thr
                85                  90                  95

Asn Thr Thr Ala Asn Thr Ala Asn Phe Val Lys Pro Thr Thr Thr
            100                 105                 110

Ser Glu Gln Ala Lys Thr Asp Asn Ser Asp Lys Ile Ile Thr Thr Ser
        115                 120                 125

Lys Ala Val Asn Arg Leu Thr Ala Thr Gly Lys Phe Val Pro Ala Asn
130                 135                 140

Asn Asn Thr Ala His Pro Lys Thr Val Thr Asp Lys Ile Val Pro Ile
145                 150                 155                 160

Lys Pro Lys Ile Gly Lys Leu Lys Gln Pro Ser Ser Leu Ser Gln Asp
                165                 170                 175

Asp Ile Ala Ala Leu Gly Asn Val Lys Asn Ile Arg Lys Val Asn Gly
            180                 185                 190

Lys Tyr Tyr Tyr Tyr Lys Glu Asp Gly Thr Leu Gln Lys Asn Tyr Ala
        195                 200                 205

Leu Asn Ile Asn Gly Lys Thr Phe Phe Phe Asp Glu Thr Gly Ala Leu
210                 215                 220
```

-continued

```
Ser Asn Asn Thr Leu Pro Ser Lys Lys Gly Asn Ile Thr Asn Asn Asp
225                 230                 235                 240

Asn Thr Asn Ser Phe Ala Gln Tyr Asn Gln Val Tyr Ser Thr Asp Val
            245                 250                 255

Ala Asn Phe Glu His Val Asp His Tyr Leu Thr Ala Glu Ser Trp Tyr
        260                 265                 270

Arg Pro Lys Tyr Ile Leu Lys Asp Gly Lys Thr Trp Thr Gln Ser Thr
    275                 280                 285

Glu Lys Asp Phe Arg Pro Leu Leu Met Thr Trp Trp Pro Asp Gln Glu
290                 295                 300

Thr Gln Arg Gln Tyr Val Asn Tyr Met Asn Ala Gln Leu Gly Ile His
305                 310                 315                 320

Gln Thr Tyr Asn Thr Ala Thr Ser Pro Leu Gln Leu Asn Leu Ala Ala
            325                 330                 335

Gln Thr Ile Gln Thr Lys Ile Glu Glu Lys Ile Thr Ala Glu Lys Asn
            340                 345                 350

Thr Asn Trp Leu Arg Gln Thr Ile Ser Ala Phe Val Lys Thr Gln Ser
    355                 360                 365

Ala Trp Asn Ser Asp Ser Glu Lys Pro Phe Asp Asp His Leu Gln Lys
370                 375                 380

Gly Ala Leu Leu Tyr Ser Asn Asn Ser Lys Leu Thr Ser Gln Ala Asn
385                 390                 395                 400

Ser Asn Tyr Arg Ile Leu Asn Arg Thr Pro Thr Asn Gln Thr Gly Lys
            405                 410                 415

Lys Asp Pro Arg Tyr Thr Ala Asp Arg Thr Ile Gly Gly Tyr Glu Phe
            420                 425                 430

Leu Leu Ala Asn Asp Val Asp Asn Ser Asn Pro Val Val Gln Ala Glu
            435                 440                 445

Gln Leu Asn Trp Leu His Phe Leu Met Asn Phe Gly Asn Ile Tyr Ala
    450                 455                 460

Asn Asp Pro Asp Ala Asn Phe Asp Ser Ile Arg Val Asp Ala Val Asp
465                 470                 475                 480

Asn Val Asp Ala Asp Leu Leu Gln Ile Ala Gly Asp Tyr Leu Lys Ala
            485                 490                 495

Ala Lys Gly Ile His Lys Asn Asp Lys Ala Ala Asn Asp His Leu Ser
            500                 505                 510

Ile Leu Glu Ala Trp Ser Tyr Asn Asp Thr Pro Tyr Leu His Asp Asp
            515                 520                 525

Gly Asp Asn Met Ile Asn Met Asp Asn Arg Leu Arg Leu Ser Leu Leu
530                 535                 540

Tyr Ser Leu Ala Lys Pro Leu Asn Gln Arg Ser Gly Met Asn Pro Leu
545                 550                 555                 560

Ile Thr Asn Ser Leu Val Asn Arg Thr Asp Asp Asn Ala Glu Thr Ala
            565                 570                 575

Ala Val Pro Ser Tyr Ser Phe Ile Arg Ala His Asp Ser Glu Val Gln
            580                 585                 590

Asp Leu Ile Arg Asn Ile Ile Arg Thr Glu Ile Asn Pro Asn Val Val
    595                 600                 605

Gly Tyr Ser Phe Thr Thr Glu Glu Ile Lys Lys Ala Phe Glu Ile Tyr
            610                 615                 620

Asn Lys Asp Leu Leu Ala Thr Glu Lys Lys Tyr Thr His Tyr Asn Thr
625                 630                 635                 640
```

```
Ala Leu Ser Tyr Ala Leu Leu Thr Asn Lys Ser Val Pro Arg
                645                 650             655

Val Tyr Tyr Gly Asp Met Phe Thr Asp Asp Gly Gln Tyr Met Ala His
            660             665             670

Lys Thr Ile Asn Tyr Glu Ala Ile Glu Thr Leu Leu Lys Ala Arg Ile
        675                 680             685

Lys Tyr Val Ser Gly Gly Gln Ala Met Arg Asn Gln Gln Val Gly Asn
    690             695                 700

Ser Glu Ile Ile Thr Ser Val Arg Tyr Gly Lys Gly Ala Leu Lys Ala
705             710             715                 720

Thr Asp Thr Gly Asp Arg Thr Thr Arg Thr Ser Gly Val Ala Val Ile
            725             730                 735

Glu Gly Asn Asn Pro Ser Leu Arg Leu Lys Ala Ser Asp Arg Val Val
        740             745             750

Val Asn Met Gly Ala Ala His Lys Asn Gln Ala Tyr Arg Pro Leu Leu
        755             760             765

Leu Thr Thr Asp Asn Gly Ile Lys Ala Tyr His Ser Asp Gln Glu Ala
    770             775             780

Ala Gly Leu Val Arg Tyr Thr Asn Asp Arg Gly Glu Leu Ile Phe Thr
785             790             795                 800

Ala Ala Asp Ile Lys Gly Tyr Ala Asn Pro Gln Val Ser Gly Tyr Leu
            805             810             815

Gly Val Trp Val Pro Val Gly Ala Ala Ala Asp Gln Asp Val Arg Val
            820             825             830

Ala Ala Ser Thr Ala Pro Ser Thr Asp Gly Lys Ser Val His Gln Asn
        835             840             845

Ala Ala Leu Asp Ser Arg Val Met Phe Glu Gly Phe Ser Asn Phe Gln
    850             855             860

Ala Phe Ala Thr Lys Lys Glu Glu Tyr Thr Asn Val Val Ile Ala Lys
865             870             875                 880

Asn Val Asp Lys Phe Ala Glu Trp Gly Val Thr Asp Phe Glu Met Ala
            885             890             895

Pro Gln Tyr Val Ser Ser Thr Asp Gly Ser Phe Leu Asp Ser Val Ile
            900             905             910

Gln Asn Gly Tyr Ala Phe Thr Asp Arg Tyr Asp Leu Gly Ile Ser Lys
        915             920             925

Pro Asn Lys Tyr Gly Thr Ala Asp Asp Leu Val Lys Ala Ile Lys Ala
    930             935             940

Leu His Ser Lys Gly Ile Lys Val Met Ala Asp Trp Val Pro Asp Gln
945             950             955                 960

Met Tyr Ala Leu Pro Glu Lys Glu Val Val Thr Ala Thr Arg Val Asp
            965             970             975

Lys Tyr Gly Thr Pro Val Ala Gly Ser Gln Ile Lys Asn Thr Leu Tyr
            980             985             990

Val Val Asp Gly Lys Ser Ser Gly Lys Asp Gln Gln Ala Lys Tyr Gly
        995             1000            1005

Gly Ala Phe Leu Glu Glu Leu Gln Ala Lys Tyr Pro Glu Leu Phe Ala
    1010            1015            1020

Arg Lys Gln Ile Ser Thr Gly Val Pro Met Asp Pro Ser Val Lys Ile
1025            1030            1035            1040

Lys Gln Trp Ser Ala Lys Tyr Phe Asn Gly Thr Asn Ile Leu Gly Arg
            1045            1050            1055

Gly Ala Gly Tyr Val Leu Lys Asp Gln Ala Thr Asn Thr Tyr Phe Ser
```

-continued

```
                    1060                1065                1070
Leu Val Ser Asp Asn Thr Phe Leu Pro Lys Ser Leu Val Asn Pro Asn
            1075                1080                1085
His Gly Thr Ser Ser Val Thr Gly Leu Val Phe Asp Gly Lys Gly
    1090                1095                1100
Tyr Val Tyr Tyr Ser Thr Ser Gly Asn Gln Ala Lys Asn Ala Phe Ile
1105                1110                1115                1120
Ser Leu Gly Asn Asn Trp Tyr Tyr Phe Asp Asn Asn Gly Tyr Met Val
                1125                1130                1135
Thr Gly Ala Gln Ser Ile Asn Gly Ala Asn Tyr Tyr Phe Leu Ser Asn
            1140                1145                1150
Gly Ile Gln Leu Arg Asn Ala Ile Tyr Asp Asn Gly Asn Lys Val Leu
        1155                1160                1165
Ser Tyr Tyr Gly Asn Asp Gly Arg Arg Tyr Glu Asn Gly Tyr Tyr Leu
    1170                1175                1180
Phe Gly Gln Gln Trp Arg Tyr Phe Gln Asn Gly Ile Met Ala Val Gly
1185                1190                1195                1200
Leu Thr Arg Val His Gly Ala Val Gln Tyr Phe Asp Ala Ser Gly Phe
                1205                1210                1215
Gln Ala Lys Gly Gln Phe Ile Thr Thr Ala Asp Gly Lys Leu Arg Tyr
            1220                1225                1230
Phe Asp Arg Asp Ser Gly Asn Gln Ile Ser Asn Arg Phe Val Arg Asn
        1235                1240                1245
Ser Lys Gly Glu Trp Phe Leu Phe Asp His Asn Gly Val Ala Val Thr
    1250                1255                1260
Gly Thr Val Thr Phe Asn Gly Gln Arg Leu Tyr Phe Lys Pro Asn Gly
1265                1270                1275                1280
Val Gln Ala Lys Gly Glu Phe Ile Arg Asp Ala Asn Gly Tyr Leu Arg
                1285                1290                1295
Tyr Tyr Asp Pro Asn Ser Gly Asn Glu Val Arg Asn Arg Phe Val Arg
            1300                1305                1310
Asn Ser Lys Gly Glu Trp Phe Leu Phe Asp His Asn Gly Ile Ala Val
        1315                1320                1325
Thr Gly Ala Arg Val Val Asn Gly His Ala Ser Ile Leu Ser Leu Met
    1330                1335                1340
Val Phe Arg Leu Arg Glu Ser Ser Leu Gln Ser Val Lys Val Val Ser
1345                1350                1355                1360
Asn Thr Met Ile Leu Ile Pro Glu Met Lys Phe Val Ile Val Met
                1365                1370                1375
```

<210> SEQ ID NO 5
<211> LENGTH: 4310
<212> TYPE: DNA
<213> ORGANISM: streptococcus mutans
<220> FEATURE:
<221> NAME/KEY: CDS
<222> LOCATION: (5)...(4295)

<400> SEQUENCE: 5

```
tttt atg gaa acc aaa cga cgt tac aaa atg cac aag gtt aaa aag cac     49
     Met Glu Thr Lys Arg Arg Tyr Lys Met His Lys Val Lys Lys His
     1               5                  10                  15 tgg gta acc gtt gct gtc gct tct ggt ttg att acc ttg ggg acc aca     97
Trp Val Thr Val Ala Val Ala Ser Gly Leu Ile Thr Leu Gly Thr Thr
            20                  25                  30 aca ctg gga agc tca gtt tca gca gaa aca gaa cag cag acc tca gat    145
```

-continued

```
Thr Leu Gly Ser Ser Val Ser Ala Glu Thr Glu Gln Gln Thr Ser Asp
             35                  40                  45 aaa gtg gta act cag aaa agt gag gat gat aag gcg gca tct gaa tcc        193
Lys Val Val Thr Gln Lys Ser Glu Asp Asp Lys Ala Ala Ser Glu Ser
         50                  55                  60 agc caa aca gat gca cct aaa act aag caa gca caa aca gaa caa acg        241
Ser Gln Thr Asp Ala Pro Lys Thr Lys Gln Ala Gln Thr Glu Gln Thr
 65                  70                  75 cag gcc caa agt cag gca aac gtt gct gat aca agc act agc ata act        289
Gln Ala Gln Ser Gln Ala Asn Val Ala Asp Thr Ser Thr Ser Ile Thr
     80                  85                  90                  95 aag gaa act cct tca caa aat att aca aca caa gcc aac tct gat gac        337
Lys Glu Thr Pro Ser Gln Asn Ile Thr Thr Gln Ala Asn Ser Asp Asp
                100                 105                 110 aaa aca gta aca aat acg aaa tca gaa gaa gca caa act tct gaa gag        385
Lys Thr Val Thr Asn Thr Lys Ser Glu Glu Ala Gln Thr Ser Glu Glu
            115                 120                 125 cgc aca aag caa tca gaa gaa gca cag act act gct tcc agt cag gct        433
Arg Thr Lys Gln Ser Glu Glu Ala Gln Thr Thr Ala Ser Ser Gln Ala
        130                 135                 140 tta aca cag gca aaa gct gaa tta aca aag caa aga caa aca gca gct        481
Leu Thr Gln Ala Lys Ala Glu Leu Thr Lys Gln Arg Gln Thr Ala Ala
    145                 150                 155 caa gaa aat aaa aat cct gtt gac tta gcg gcc att cca aat gtg aaa        529
Gln Glu Asn Lys Asn Pro Val Asp Leu Ala Ala Ile Pro Asn Val Lys
160                 165                 170                 175 caa att gat ggc aaa tat tat tat att ggt tct gat ggt cag cct aag        577
Gln Ile Asp Gly Lys Tyr Tyr Tyr Ile Gly Ser Asp Gly Gln Pro Lys
                180                 185                 190 aaa aat ttt gct cta acc gtt aat aac aaa gta ctc tac ttc gat aaa        625
Lys Asn Phe Ala Leu Thr Val Asn Asn Lys Val Leu Tyr Phe Asp Lys
            195                 200                 205 aat aca ggt gcc tta acg gac act tct cag tat caa ttt aaa caa ggg        673
Asn Thr Gly Ala Leu Thr Asp Thr Ser Gln Tyr Gln Phe Lys Gln Gly
        210                 215                 220 tta aca aaa tta aac aac gat tat act ccc cac aat caa att gtc aat        721
Leu Thr Lys Leu Asn Asn Asp Tyr Thr Pro His Asn Gln Ile Val Asn
    225                 230                 235 ttt gaa aat acc agt ctt gaa acg att gat aac tat gtc aca gct gat        769
Phe Glu Asn Thr Ser Leu Glu Thr Ile Asp Asn Tyr Val Thr Ala Asp
240                 245                 250                 255 tcg tgg tat cgt cct aag gat att tta aag aat ggc aaa acg tgg aca        817
Ser Trp Tyr Arg Pro Lys Asp Ile Leu Lys Asn Gly Lys Thr Trp Thr
                260                 265                 270 gct tca tct gag tct gat ctt cgt ccg ctt tta atg tct tgg tgg cca        865
Ala Ser Ser Glu Ser Asp Leu Arg Pro Leu Leu Met Ser Trp Trp Pro
            275                 280                 285 gat aaa caa acg caa att gct tat ctt aac tac atg aac cag caa gga        913
Asp Lys Gln Thr Gln Ile Ala Tyr Leu Asn Tyr Met Asn Gln Gln Gly
        290                 295                 300 ctt gga act ggt gaa aat tac aca gca gac agc agc caa gaa agt ctc        961
Leu Gly Thr Gly Glu Asn Tyr Thr Ala Asp Ser Ser Gln Glu Ser Leu
    305                 310                 315 aac ctt gct gca caa acc gtt caa gtt aag att gaa act aaa att tct       1009
Asn Leu Ala Ala Gln Thr Val Gln Val Lys Ile Glu Thr Lys Ile Ser
320                 325                 330                 335 caa acg cag caa acc cag tgg ctg cgt gat att atc aat agt ttt gtt       1057
Gln Thr Gln Gln Thr Gln Trp Leu Arg Asp Ile Ile Asn Ser Phe Val
                340                 345                 350
```

-continued

| | |
|---|---|
| aaa acg caa cca aat tgg aat agt caa aca gaa tcg gat act tca gct<br>Lys Thr Gln Pro Asn Trp Asn Ser Gln Thr Glu Ser Asp Thr Ser Ala<br>355 360 365 | 1105 |
| ggt gaa aaa gat cac ttg caa ggc ggt gct ctg ctt tat agc aac agc<br>Gly Glu Lys Asp His Leu Gln Gly Gly Ala Leu Leu Tyr Ser Asn Ser<br>370 375 380 | 1153 |
| gat aag aca gcc tat gct aat tcc gat tac cgt ctt ttg aac cgc aca<br>Asp Lys Thr Ala Tyr Ala Asn Ser Asp Tyr Arg Leu Leu Asn Arg Thr<br>385 390 395 | 1201 |
| cca acc agt caa acg ggt aaa cca aaa tat ttt gaa gac aat tct tct<br>Pro Thr Ser Gln Thr Gly Lys Pro Lys Tyr Phe Glu Asp Asn Ser Ser<br>400 405 410 415 | 1249 |
| ggt ggc tat gac ttc ctc cta gct aat gat att gat aat tca aat cca<br>Gly Gly Tyr Asp Phe Leu Leu Ala Asn Asp Ile Asp Asn Ser Asn Pro<br>420 425 430 | 1297 |
| gtg gtt caa gct gaa caa tta aac tgg ctt cat tat ctg atg aat tat<br>Val Val Gln Ala Glu Gln Leu Asn Trp Leu His Tyr Leu Met Asn Tyr<br>435 440 445 | 1345 |
| ggt tct att gtc gct aat gat cct gag gct aat ttt gac ggt gtt cgt<br>Gly Ser Ile Val Ala Asn Asp Pro Glu Ala Asn Phe Asp Gly Val Arg<br>450 455 460 | 1393 |
| gtt gat gcc gtt gat aat gtt aat gcc gac ttg ctg cag att gct tcg<br>Val Asp Ala Val Asp Asn Val Asn Ala Asp Leu Leu Gln Ile Ala Ser<br>465 470 475 | 1441 |
| gac tat ttg aaa gcc cat tat ggt gtt gat aag agt gag aaa aat gcg<br>Asp Tyr Leu Lys Ala His Tyr Gly Val Asp Lys Ser Glu Lys Asn Ala<br>480 485 490 495 | 1489 |
| att aat cat ctt tcc att tta gaa gct tgg tca gat aat gat ccc caa<br>Ile Asn His Leu Ser Ile Leu Glu Ala Trp Ser Asp Asn Asp Pro Gln<br>500 505 510 | 1537 |
| tac aat aaa gat act aag ggt gca caa tta ccg att gat aat aaa ctg<br>Tyr Asn Lys Asp Thr Lys Gly Ala Gln Leu Pro Ile Asp Asn Lys Leu<br>515 520 525 | 1585 |
| cgc cta tcg ctt tta tat gct ttg acg cgt cct ctt gaa aaa gat gca<br>Arg Leu Ser Leu Leu Tyr Ala Leu Thr Arg Pro Leu Glu Lys Asp Ala<br>530 535 540 | 1633 |
| agc aat aaa aat gaa att cgc agc gga ctt gag cct gtc ata aca aat<br>Ser Asn Lys Asn Glu Ile Arg Ser Gly Leu Glu Pro Val Ile Thr Asn<br>545 550 555 | 1681 |
| agc ttg aat aac cgt tca gct gaa ggt aaa aat agt gaa cgt atg gct<br>Ser Leu Asn Asn Arg Ser Ala Glu Gly Lys Asn Ser Glu Arg Met Ala<br>560 565 570 575 | 1729 |
| aac tat att ttt atc cgc gct cac gac agt gaa gtc caa acg gtt att<br>Asn Tyr Ile Phe Ile Arg Ala His Asp Ser Glu Val Gln Thr Val Ile<br>580 585 590 | 1777 |
| gct aaa att att aaa gct cag att aat ccc aaa aca gat ggt ttg acc<br>Ala Lys Ile Ile Lys Ala Gln Ile Asn Pro Lys Thr Asp Gly Leu Thr<br>595 600 605 | 1825 |
| ttt act ttg gat gaa ttg aag caa gcc ttt aag atc tac aat gaa gac<br>Phe Thr Leu Asp Glu Leu Lys Gln Ala Phe Lys Ile Tyr Asn Glu Asp<br>610 615 620 | 1873 |
| atg cgt cag gct aag aaa aag tac aca caa tcc aat att ccg aca gcc<br>Met Arg Gln Ala Lys Lys Lys Tyr Thr Gln Ser Asn Ile Pro Thr Ala<br>625 630 635 | 1921 |
| tat gct ttg atg ctg tcc aat aaa gat tct att aca cgt ctt tat tat<br>Tyr Ala Leu Met Leu Ser Asn Lys Asp Ser Ile Thr Arg Leu Tyr Tyr<br>640 645 650 655 | 1969 |
| ggt gat atg tac agt gat gac ggt caa tat atg gcg act aaa tcc cct<br>Gly Asp Met Tyr Ser Asp Asp Gly Gln Tyr Met Ala Thr Lys Ser Pro<br>660 665 670 | 2017 |

-continued

```
tat tat gat gct att gat act tta tta aag gca cgt att aaa tat gcc    2065
Tyr Tyr Asp Ala Ile Asp Thr Leu Leu Lys Ala Arg Ile Lys Tyr Ala
            675                 680                 685 gcc ggt ggt caa gac atg aag atc acc tat gtt gaa ggt gat aaa agt    2113
Ala Gly Gly Gln Asp Met Lys Ile Thr Tyr Val Glu Gly Asp Lys Ser
        690                 695                 700 cat atg gat tgg gat tat aca ggc gtt ttg act tct gtt cgt tat ggt    2161
His Met Asp Trp Asp Tyr Thr Gly Val Leu Thr Ser Val Arg Tyr Gly
    705                 710                 715 aca gga gct aat gaa gct aca gat caa ggc agt gaa gca act aaa aca    2209
Thr Gly Ala Asn Glu Ala Thr Asp Gln Gly Ser Glu Ala Thr Lys Thr
720                 725                 730                 735 caa gga atg gct gtc att acc agc aat aac cct agc ctt aaa ttg aat    2257
Gln Gly Met Ala Val Ile Thr Ser Asn Asn Pro Ser Leu Lys Leu Asn
                740                 745                 750 caa aat gat aaa gta att gtc aat atg ggg gct gcg cat aaa aat caa    2305
Gln Asn Asp Lys Val Ile Val Asn Met Gly Ala Ala His Lys Asn Gln
            755                 760                 765 gag tac cgt ccg ctc ctc tta aca act aaa gat ggt ttg aca agc tac    2353
Glu Tyr Arg Pro Leu Leu Leu Thr Thr Lys Asp Gly Leu Thr Ser Tyr
        770                 775                 780 act tct gat gcc gct gct aaa tcc ctt tat cgc aaa acg aat gat aaa    2401
Thr Ser Asp Ala Ala Ala Lys Ser Leu Tyr Arg Lys Thr Asn Asp Lys
    785                 790                 795 gga gaa tta gtc ttt gat gct agt gac att caa ggt tac ctg aat ccg    2449
Gly Glu Leu Val Phe Asp Ala Ser Asp Ile Gln Gly Tyr Leu Asn Pro
800                 805                 810                 815 caa gta tca ggt tat tta gcc gtt tgg gtt cca gta gga gct agt gat    2497
Gln Val Ser Gly Tyr Leu Ala Val Trp Val Pro Val Gly Ala Ser Asp
                820                 825                 830 aat caa gat gtt cgt gta gca gca agc aat aag gca aat gct act ggt    2545
Asn Gln Asp Val Arg Val Ala Ala Ser Asn Lys Ala Asn Ala Thr Gly
            835                 840                 845 caa gtc tac gaa tca tca agt gct ctt gat tct caa ttg att tac gaa    2593
Gln Val Tyr Glu Ser Ser Ser Ala Leu Asp Ser Gln Leu Ile Tyr Glu
        850                 855                 860 ggt ttc tca aac ttc caa gat ttt gta acg aaa gat tca gac tat act    2641
Gly Phe Ser Asn Phe Gln Asp Phe Val Thr Lys Asp Ser Asp Tyr Thr
    865                 870                 875 aat aag aag att gct caa aat gtc caa ctc ttc aaa tct tgg ggt gtc    2689
Asn Lys Lys Ile Ala Gln Asn Val Gln Leu Phe Lys Ser Trp Gly Val
880                 885                 890                 895 act tcc ttt gaa atg gca ccg caa tat gtc tct tct gaa gat ggt tct    2737
Thr Ser Phe Glu Met Ala Pro Gln Tyr Val Ser Ser Glu Asp Gly Ser
                900                 905                 910 ttt cta gac tct att att caa aat ggt tat gcc ttt gag gat cgt tat    2785
Phe Leu Asp Ser Ile Ile Gln Asn Gly Tyr Ala Phe Glu Asp Arg Tyr
            915                 920                 925 gat ctt gct atg agt aag aat aac aaa tac ggt tct cag caa gac atg    2833
Asp Leu Ala Met Ser Lys Asn Asn Lys Tyr Gly Ser Gln Gln Asp Met
        930                 935                 940 att aat gca gtt aaa gct ctg cat aaa agc ggt att cag gtt att gcg    2881
Ile Asn Ala Val Lys Ala Leu His Lys Ser Gly Ile Gln Val Ile Ala
    945                 950                 955 gat tgg gta cca gat caa atc tat aat ctt ccg ggc aaa gaa gtc gta    2929
Asp Trp Val Pro Asp Gln Ile Tyr Asn Leu Pro Gly Lys Glu Val Val
960                 965                 970                 975 acg gct aca cgt gtc aac gat tat ggt gag tat cgc aaa gac tct gaa    2977
Thr Ala Thr Arg Val Asn Asp Tyr Gly Glu Tyr Arg Lys Asp Ser Glu
```

|   |   |   |
|---|---|---|
| 980 | 985 | 990 |

| | |
|---|---|
| atc aaa aat aca ctc tat gct gcc aac act aag agt aat ggt aag gat<br>Ile Lys Asn Thr Leu Tyr Ala Ala Asn Thr Lys Ser Asn Gly Lys Asp<br>　　　　995　　　　　　　　1000　　　　　　　　1005 | 3025 |
| tat caa gcg aag tat ggc ggt gct ttc ctt agt gaa ctc gct gct aag<br>Tyr Gln Ala Lys Tyr Gly Gly Ala Phe Leu Ser Glu Leu Ala Ala Lys<br>　　1010　　　　　　　　1015　　　　　　　　1020 | 3073 |
| tac cct agt atc ttt aac cgc acg caa att tca aat ggt aag aag att<br>Tyr Pro Ser Ile Phe Asn Arg Thr Gln Ile Ser Asn Gly Lys Lys Ile<br>1025　　　　　　　　1030　　　　　　　　1035 | 3121 |
| gat cca agc gaa aaa atc aca gca tgg aaa gca aaa tac ttc aat ggg<br>Asp Pro Ser Glu Lys Ile Thr Ala Trp Lys Ala Lys Tyr Phe Asn Gly<br>1040　　　　　　　　1045　　　　　　　　1050　　　　　　　　1055 | 3169 |
| aca aat att cta ggc cgt ggt gtt ggt tat gtt ctt aaa gat aat gct<br>Thr Asn Ile Leu Gly Arg Gly Val Gly Tyr Val Leu Lys Asp Asn Ala<br>　　　　　　　　1060　　　　　　　　1065　　　　　　　　1070 | 3217 |
| agt gat aaa tac ttt gaa ctg aaa ggg aat caa acc tat ctg cca aaa<br>Ser Asp Lys Tyr Phe Glu Leu Lys Gly Asn Gln Thr Tyr Leu Pro Lys<br>　　　　1075　　　　　　　　1080　　　　　　　　1085 | 3265 |
| cag atg act aac aaa gaa gct tcg act ggt ttt gtt aat gat ggc aat<br>Gln Met Thr Asn Lys Glu Ala Ser Thr Gly Phe Val Asn Asp Gly Asn<br>　　　　　　　　1090　　　　　　　　1095　　　　　　　　1100 | 3313 |
| ggg atg act ttc tat tca act agt ggt tat caa gcc aag aac agc ttt<br>Gly Met Thr Phe Tyr Ser Thr Ser Gly Tyr Gln Ala Lys Asn Ser Phe<br>1105　　　　　　　　1110　　　　　　　　1115 | 3361 |
| gtt caa gat gcc aaa gga aac tgg tat tac ttt gat aat aat ggc cat<br>Val Gln Asp Ala Lys Gly Asn Trp Tyr Tyr Phe Asp Asn Asn Gly His<br>1120　　　　　　　　1125　　　　　　　　1130　　　　　　　　1135 | 3409 |
| atg gtt tat ggc tta cag cag cta aat ggc gaa gtg caa tac ttt tta<br>Met Val Tyr Gly Leu Gln Gln Leu Asn Gly Glu Val Gln Tyr Phe Leu<br>　　　　　　　　1140　　　　　　　　1145　　　　　　　　1150 | 3457 |
| tca aat ggt gtt caa ttg cgt gaa tct ttc ttg gaa aac gct gat ggc<br>Ser Asn Gly Val Gln Leu Arg Glu Ser Phe Leu Glu Asn Ala Asp Gly<br>　　　　1155　　　　　　　　1160　　　　　　　　1165 | 3505 |
| agc aag aac tat ttt ggt cat cta gga aat aga tat agt aat ggt tat<br>Ser Lys Asn Tyr Phe Gly His Leu Gly Asn Arg Tyr Ser Asn Gly Tyr<br>　　　　　　　　1170　　　　　　　　1175　　　　　　　　1180 | 3553 |
| tat tca ttt gat aat gat agt aag tgg cgt tat ttt gat gcc agt gga<br>Tyr Ser Phe Asp Asn Asp Ser Lys Trp Arg Tyr Phe Asp Ala Ser Gly<br>　　　　　　　　1185　　　　　　　　1190　　　　　　　　1195 | 3601 |
| gtc atg gct gta ggt ttg aaa aca att aac ggc aat acg cag tac ttt<br>Val Met Ala Val Gly Leu Lys Thr Ile Asn Gly Asn Thr Gln Tyr Phe<br>1200　　　　　　　　1205　　　　　　　　1210　　　　　　　　1215 | 3649 |
| gat caa gat ggt tat caa gtc aaa ggt gct tgg ata aca ggc agc gat<br>Asp Gln Asp Gly Tyr Gln Val Lys Gly Ala Trp Ile Thr Gly Ser Asp<br>　　　　　　　　1220　　　　　　　　1225　　　　　　　　1230 | 3697 |
| ggc aaa aag cgt tat ttt gat gac gga tct gga aat atg gct gtt aat<br>Gly Lys Lys Arg Tyr Phe Asp Asp Gly Ser Gly Asn Met Ala Val Asn<br>　　　　　　　　1235　　　　　　　　1240　　　　　　　　1245 | 3745 |
| cgt ttt gca aat gat aaa aac ggc gat tgg tac tat ctc aat tca gat<br>Arg Phe Ala Asn Asp Lys Asn Gly Asp Trp Tyr Tyr Leu Asn Ser Asp<br>　　　　1250　　　　　　　　1255　　　　　　　　1260 | 3793 |
| ggc att gcc ttg gtt ggt gtc caa acc att aat ggt aag act tat tac<br>Gly Ile Ala Leu Val Gly Val Gln Thr Ile Asn Gly Lys Thr Tyr Tyr<br>1265　　　　　　　　1270　　　　　　　　1275 | 3841 |
| ttt ggc caa gat ggt aag caa atc aaa ggt aaa att att aca gac aat<br>Phe Gly Gln Asp Gly Lys Gln Ile Lys Gly Lys Ile Ile Thr Asp Asn<br>1280　　　　　　　　1285　　　　　　　　1290　　　　　　　　1295 | 3889 |
| ggt aag ctg aaa tat ttc ctt gcc aat tca gga gaa tta gca cgc aat | 3937 |

```
Gly Lys Leu Lys Tyr Phe Leu Ala Asn Ser Gly Glu Leu Ala Arg Asn
                1300                1305                1310 atc ttt gca aca gac agt caa aac aat tgg tat tac ttt ggt tca gac      3985
Ile Phe Ala Thr Asp Ser Gln Asn Asn Trp Tyr Tyr Phe Gly Ser Asp
                1315                1320                1325 ggt gtt gcg gtt aca ggc agt cag aca att gct ggt aaa aag ctc tat      4033
Gly Val Ala Val Thr Gly Ser Gln Thr Ile Ala Gly Lys Lys Leu Tyr
                1330                1335                1340 ttt gca agc gac gga aaa caa gtc aaa ggc agc ttt gtc act tat aat      4081
Phe Ala Ser Asp Gly Lys Gln Val Lys Gly Ser Phe Val Thr Tyr Asn
                1345                1350                1355 ggt aaa gtt cat tat tat cat gct gac tca gga gaa tta caa gtt aac      4129
Gly Lys Val His Tyr Tyr His Ala Asp Ser Gly Glu Leu Gln Val Asn
1360                1365                1370                1375 cgc ttt gaa gca gat aag gat ggt aat tgg tat tat ctt gat tca aat      4177
Arg Phe Glu Ala Asp Lys Asp Gly Asn Trp Tyr Tyr Leu Asp Ser Asn
                1380                1385                1390 ggt gaa gct ctg aca ggt agc caa cgc att aac gat cag cgt gtc ttc      4225
Gly Glu Ala Leu Thr Gly Ser Gln Arg Ile Asn Asp Gln Arg Val Phe
                1395                1400                1405 ttt acg cga gaa gga aaa caa gtt aaa ggt gat gtt gct tat gat gag      4273
Phe Thr Arg Glu Gly Lys Gln Val Lys Gly Asp Val Ala Tyr Asp Glu
                1410                1415                1420 cga agg ctt ctc gta tat aga t aagatagtgg taaca                        4310
Arg Arg Leu Leu Val Tyr Arg
                1425            1430

<210> SEQ ID NO 6
<211> LENGTH: 1430
<212> TYPE: PRT
<213> ORGANISM: streptococcus mutans

<400> SEQUENCE: 6

Met Glu Thr Lys Arg Arg Tyr Lys Met His Lys Val Lys His Trp
1               5                   10                  15

Val Thr Val Ala Val Ala Ser Gly Leu Ile Thr Leu Gly Thr Thr Thr
            20                  25                  30

Leu Gly Ser Ser Val Ser Ala Glu Thr Glu Gln Gln Thr Ser Asp Lys
        35                  40                  45

Val Val Thr Gln Lys Ser Glu Asp Lys Ala Ala Ser Glu Ser Ser
    50                  55                  60

Gln Thr Asp Ala Pro Lys Thr Lys Gln Ala Gln Thr Glu Gln Thr Gln
65                  70                  75                  80

Ala Gln Ser Gln Ala Asn Val Ala Asp Thr Ser Thr Ser Ile Thr Lys
                85                  90                  95

Glu Thr Pro Ser Gln Asn Ile Thr Thr Gln Ala Asn Ser Asp Asp Lys
            100                 105                 110

Thr Val Thr Asn Thr Lys Ser Glu Glu Ala Gln Thr Ser Glu Glu Arg
        115                 120                 125

Thr Lys Gln Ser Glu Glu Ala Gly Thr Thr Ala Ser Ser Gln Ala Leu
    130                 135                 140

Thr Gln Ala Lys Ala Glu Leu Thr Lys Gln Arg Gln Thr Ala Ala Gln
145                 150                 155                 160

Glu Asn Lys Asn Pro Val Asp Leu Ala Ala Ile Pro Asn Val Lys Gln
                165                 170                 175

Ile Asp Gly Lys Tyr Tyr Tyr Ile Gly Ser Asp Gly Gln Pro Lys Lys
            180                 185                 190
```

-continued

```
Asn Phe Ala Leu Thr Val Asn Asn Lys Val Leu Tyr Phe Asp Lys Asn
            195                 200                 205

Thr Gly Ala Leu Thr Asp Thr Ser Gln Tyr Gln Phe Lys Gln Gly Leu
    210                 215                 220

Thr Lys Leu Asn Asn Asp Tyr Thr Pro His Asn Gln Ile Val Asn Phe
225                 230                 235                 240

Glu Asn Thr Ser Leu Glu Thr Ile Asp Asn Tyr Val Thr Ala Asp Ser
                245                 250                 255

Trp Tyr Arg Pro Lys Asp Ile Leu Lys Asn Gly Lys Thr Trp Thr Ala
            260                 265                 270

Ser Ser Glu Ser Asp Leu Arg Pro Leu Leu Met Ser Trp Trp Pro Asp
    275                 280                 285

Lys Gln Thr Gln Ile Ala Tyr Leu Asn Tyr Met Asn Gln Gln Gly Leu
290                 295                 300

Gly Thr Gly Glu Asn Tyr Thr Ala Asp Ser Ser Gln Glu Ser Leu Asn
305                 310                 315                 320

Leu Ala Ala Gln Thr Val Gln Val Lys Ile Glu Thr Lys Ile Ser Gln
                325                 330                 335

Thr Gln Gln Thr Gln Trp Leu Arg Asp Ile Ile Asn Ser Phe Val Lys
            340                 345                 350

Thr Gln Pro Asn Trp Asn Ser Gln Thr Glu Ser Asp Thr Ser Ala Gly
    355                 360                 365

Glu Lys Asp His Leu Gln Gly Gly Ala Leu Leu Tyr Ser Asn Ser Asp
370                 375                 380

Lys Thr Ala Tyr Ala Asn Ser Asp Tyr Arg Leu Leu Asn Arg Thr Pro
385                 390                 395                 400

Thr Ser Gln Thr Gly Lys Pro Lys Tyr Phe Glu Asp Asn Ser Ser Gly
                405                 410                 415

Gly Tyr Asp Phe Leu Leu Ala Asn Asp Ile Asp Asn Ser Asn Pro Val
            420                 425                 430

Val Gln Ala Glu Gln Leu Asn Trp Leu His Tyr Leu Met Asn Tyr Gly
    435                 440                 445

Ser Ile Val Ala Asn Asp Pro Glu Ala Asn Phe Asp Gly Val Arg Val
450                 455                 460

Asp Ala Val Asp Asn Val Asn Ala Asp Leu Leu Gln Ile Ala Ser Asp
465                 470                 475                 480

Tyr Leu Lys Ala His Tyr Gly Val Asp Lys Ser Glu Lys Asn Ala Ile
                485                 490                 495

Asn His Leu Ser Ile Leu Glu Ala Trp Ser Asp Asn Asp Pro Gln Tyr
            500                 505                 510

Asn Lys Asp Thr Lys Gly Ala Gln Leu Pro Ile Asp Asn Lys Leu Arg
    515                 520                 525

Leu Ser Leu Leu Tyr Ala Leu Thr Arg Pro Leu Glu Lys Asp Ala Ser
530                 535                 540

Asn Lys Asn Glu Ile Arg Ser Gly Leu Glu Pro Val Ile Thr Asn Ser
545                 550                 555                 560

Leu Asn Asn Arg Ser Ala Glu Gly Lys Asn Ser Glu Arg Met Ala Asn
                565                 570                 575

Tyr Ile Phe Ile Arg Ala His Asp Ser Glu Val Gln Thr Val Ile Ala
            580                 585                 590

Lys Ile Ile Lys Ala Gln Ile Asn Pro Lys Thr Asp Gly Leu Thr Phe
    595                 600                 605

Thr Leu Asp Glu Leu Lys Gln Ala Phe Lys Ile Tyr Asn Glu Asp Met
```

```
              610                 615                 620
Arg Gln Ala Lys Lys Tyr Thr Gln Ser Asn Ile Pro Thr Ala Tyr
625                 630                 635                 640

Ala Leu Met Leu Ser Asn Lys Asp Ser Ile Thr Arg Leu Tyr Tyr Gly
                    645                 650                 655

Asp Met Tyr Ser Asp Asp Gly Gln Tyr Met Ala Thr Lys Ser Pro Tyr
                660                 665                 670

Tyr Asp Ala Ile Asp Thr Leu Leu Lys Ala Arg Ile Lys Tyr Ala Ala
                    675                 680                 685

Gly Gly Gln Asp Met Lys Ile Thr Tyr Val Glu Gly Asp Lys Ser His
                690                 695                 700

Met Asp Trp Asp Tyr Thr Gly Val Leu Thr Ser Val Arg Tyr Gly Thr
705                 710                 715                 720

Gly Ala Asn Glu Ala Thr Asp Gln Gly Ser Glu Ala Thr Lys Thr Gln
                    725                 730                 735

Gly Met Ala Val Ile Thr Ser Asn Asn Pro Ser Leu Lys Leu Asn Gln
                    740                 745                 750

Asn Asp Lys Val Ile Val Asn Met Gly Ala Ala His Lys Asn Gln Glu
                755                 760                 765

Tyr Arg Pro Leu Leu Leu Thr Thr Lys Asp Gly Leu Thr Ser Tyr Thr
770                 775                 780

Ser Asp Ala Ala Lys Ser Leu Tyr Arg Lys Thr Asn Asp Lys Gly
785                 790                 795                 800

Glu Leu Val Phe Asp Ala Ser Asp Ile Gln Gly Tyr Leu Asn Pro Gln
                    805                 810                 815

Val Ser Gly Tyr Leu Ala Val Trp Val Pro Val Gly Ala Ser Asp Asn
                820                 825                 830

Gln Asp Val Arg Val Ala Ala Ser Asn Lys Ala Asn Ala Thr Gly Gln
                835                 840                 845

Val Tyr Glu Ser Ser Ser Ala Leu Asp Ser Gln Leu Ile Tyr Glu Gly
                850                 855                 860

Phe Ser Asn Phe Gln Asp Phe Val Thr Lys Asp Ser Asp Tyr Thr Asn
865                 870                 875                 880

Lys Lys Ile Ala Gln Asn Val Gln Leu Phe Lys Ser Trp Gly Val Thr
                    885                 890                 895

Ser Phe Glu Met Ala Pro Gln Tyr Val Ser Ser Glu Asp Gly Ser Phe
                900                 905                 910

Leu Asp Ser Ile Ile Gln Asn Gly Tyr Ala Phe Glu Asp Arg Tyr Asp
                915                 920                 925

Leu Ala Met Ser Lys Asn Asn Lys Tyr Gly Ser Gln Gln Asp Met Ile
                930                 935                 940

Asn Ala Val Lys Ala Leu His Lys Ser Gly Ile Gln Val Ile Ala Asp
945                 950                 955                 960

Trp Val Pro Asp Gln Ile Tyr Asn Leu Pro Gly Lys Glu Val Val Thr
                    965                 970                 975

Ala Thr Arg Val Asn Asp Tyr Gly Glu Tyr Arg Lys Asp Ser Glu Ile
                    980                 985                 990

Lys Asn Thr Leu Tyr Ala Ala Asn Thr Lys Ser Asn Gly Lys Asp Tyr
                995                 1000                1005

Gln Ala Lys Tyr Gly Gly Ala Phe Leu Ser Glu Leu Ala Ala Lys Tyr
                1010                1015                1020

Pro Ser Ile Phe Asn Arg Thr Gln Ile Ser Asn Gly Lys Lys Ile Asp
1025                1030                1035                1040
```

-continued

```
Pro Ser Glu Lys Ile Thr Ala Trp Lys Ala Lys Tyr Phe Asn Gly Thr
            1045                1050                1055
Asn Ile Leu Gly Arg Gly Val Gly Tyr Val Leu Lys Asp Asn Ala Ser
            1060                1065                1070
Asp Lys Tyr Phe Glu Leu Lys Gly Asn Gln Thr Tyr Leu Pro Lys Gln
            1075                1080                1085
Met Thr Asn Lys Glu Ala Ser Thr Gly Phe Val Asn Asp Gly Asn Gly
            1090                1095                1100
Met Thr Phe Tyr Ser Thr Ser Gly Tyr Gln Ala Lys Asn Ser Phe Val
1105                1110                1115                1120
Gln Asp Ala Lys Gly Asn Trp Tyr Tyr Phe Asp Asn Asn Gly His Met
            1125                1130                1135
Val Tyr Gly Leu Gln Gln Leu Asn Gly Glu Val Gln Tyr Phe Leu Ser
            1140                1145                1150
Asn Gly Val Gln Leu Arg Glu Ser Phe Leu Glu Asn Ala Asp Gly Ser
            1155                1160                1165
Lys Asn Tyr Phe Gly His Leu Gly Asn Arg Tyr Ser Asn Gly Tyr Tyr
            1170                1175                1180
Ser Phe Asp Asn Asp Ser Lys Trp Arg Tyr Phe Asp Ala Ser Gly Val
1185                1190                1195                1200
Met Ala Val Gly Leu Lys Thr Ile Asn Gly Asn Thr Gln Tyr Phe Asp
            1205                1210                1215
Gln Asp Gly Tyr Gln Val Lys Gly Ala Trp Ile Thr Gly Ser Asp Gly
            1220                1225                1230
Lys Lys Arg Tyr Phe Asp Asp Gly Ser Gly Asn Met Ala Val Asn Arg
            1235                1240                1245
Phe Ala Asn Asp Lys Asn Gly Asp Trp Tyr Tyr Leu Asn Ser Asp Gly
            1250                1255                1260
Ile Ala Leu Val Gly Val Gln Thr Ile Asn Gly Lys Thr Tyr Tyr Phe
1265                1270                1275                1280
Gly Gln Asp Gly Lys Gln Ile Lys Gly Lys Ile Ile Thr Asp Asn Gly
            1285                1290                1295
Lys Leu Lys Tyr Phe Leu Ala Asn Ser Gly Glu Leu Ala Arg Asn Ile
            1300                1305                1310
Phe Ala Thr Asp Ser Gln Asn Asn Trp Tyr Tyr Phe Gly Ser Asp Gly
            1315                1320                1325
Val Ala Val Thr Gly Ser Gln Thr Ile Ala Gly Lys Lys Leu Tyr Phe
            1330                1335                1340
Ala Ser Asp Gly Lys Gln Val Lys Gly Ser Phe Val Thr Tyr Asn Gly
1345                1350                1355                1360
Lys Val His Tyr Tyr His Ala Asp Ser Gly Glu Leu Gln Val Asn Arg
            1365                1370                1375
Phe Glu Ala Asp Lys Asp Gly Asn Trp Tyr Tyr Leu Asp Ser Asn Gly
            1380                1385                1390
Glu Ala Leu Thr Gly Ser Gln Arg Ile Asn Asp Gln Arg Val Phe Phe
            1395                1400                1405
Thr Arg Glu Gly Lys Gln Val Lys Gly Asp Val Ala Tyr Asp Glu Arg
            1410                1415                1420
Arg Leu Leu Val Tyr Arg
1425                1430
```